(12) United States Patent
Ota et al.

(10) Patent No.: US 11,542,461 B2
(45) Date of Patent: *Jan. 3, 2023

(54) ANALYSIS DEVICE

(71) Applicants: THE UNIVERSITY OF TOKYO, Tokyo (JP); OSAKA UNIVERSITY, Osaka (JP)

(72) Inventors: Sadao Ota, Tokyo (JP); Issei Sato, Tokyo (JP); Katsuhito Fujiu, Tokyo (JP); Satoko Yamaguchi, Tokyo (JP); Kayo Waki, Tokyo (JP); Yoko Itahashi, Tokyo (JP); Ryoichi Horisaki, Osaka (JP)

(73) Assignees: The University of Tokyo, Tokyo (JP); OSAKA UNIVERSITY, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/351,117

(22) Filed: Jun. 17, 2021

(65) Prior Publication Data

US 2022/0041963 A1 Feb. 10, 2022

Related U.S. Application Data

(63) Continuation of application No. 15/771,180, filed as application No. PCT/JP2016/082089 on Oct. 28, 2016, now Pat. No. 11,098,275.

(Continued)

(30) Foreign Application Priority Data

Oct. 28, 2015 (JP) .............................. JP2015-212356

(51) Int. Cl.
*G01N 15/14* (2006.01)
*C12M 1/34* (2006.01)
(Continued)

(52) U.S. Cl.
CPC ............... *C12M 1/34* (2013.01); *G01N 15/14* (2013.01); *G01N 15/1404* (2013.01);
(Continued)

(58) Field of Classification Search
None
See application file for complete search history.

(56) References Cited

U.S. PATENT DOCUMENTS

| 4,537,861 A | 8/1985 | Elings et al. |
| 5,483,469 A | 1/1996 | Van Den Engh et al. |

(Continued)

FOREIGN PATENT DOCUMENTS

| CN | 1330151 A | 1/2002 |
| CN | 101925809 A | 12/2010 |

(Continued)

OTHER PUBLICATIONS

CN201680011390X Chinese Search Report dated Mar. 1, 2019.
(Continued)

*Primary Examiner* — David P Porta
*Assistant Examiner* — Mamadou Faye
(74) *Attorney, Agent, or Firm* — Wilson Sonsini Goodrich & Rosati

(57) ABSTRACT

An analysis device includes an analysis unit configured to receive scattered light, transmitted light, fluorescence, or electromagnetic waves from an observed object located in a light irradiation region light-irradiated from a light source and analyze the observed object on the basis of a signal extracted on the basis of a time axis of an electrical signal output from a light-receiving unit configured to convert the received light or electromagnetic waves into the electrical signal.

20 Claims, 31 Drawing Sheets

Related U.S. Application Data

(60) Provisional application No. 62/372,321, filed on Aug. 9, 2016.

(51) Int. Cl.
  *G01N 21/01* (2006.01)
  *G01N 21/27* (2006.01)
  *G01N 21/64* (2006.01)
  *G06K 9/62* (2022.01)
  *G06K 9/00* (2022.01)
  *G06V 20/69* (2022.01)
  *G01N 21/65* (2006.01)
  *G01N 15/10* (2006.01)

(52) U.S. Cl.
  CPC ....... *G01N 15/147* (2013.01); *G01N 15/1429* (2013.01); *G01N 15/1434* (2013.01); *G01N 15/1459* (2013.01); *G01N 21/01* (2013.01); *G01N 21/27* (2013.01); *G01N 21/64* (2013.01); *G01N 21/65* (2013.01); *G06K 9/00536* (2013.01); *G06K 9/6255* (2013.01); *G06K 9/6263* (2013.01); *G06V 20/698* (2022.01); *G01N 2015/1006* (2013.01); *G01N 2015/145* (2013.01); *G01N 2015/1413* (2013.01); *G01N 2015/1415* (2013.01)

(56) References Cited

U.S. PATENT DOCUMENTS

| | | | |
|---|---|---|---|
| 6,064,473 | A | 5/2000 | Hironaga et al. |
| 7,217,573 | B1 | 5/2007 | Oshida et al. |
| 7,812,303 | B2 | 10/2010 | Meyers et al. |
| 9,360,660 | B2 | 6/2016 | Yi et al. |
| 10,761,011 | B2 | 9/2020 | Ota et al. |
| 11,054,363 | B2 | 7/2021 | Ota et al. |
| 11,098,275 | B2 * | 8/2021 | Ota ............... G01N 15/14 |
| 2002/0041376 | A1 | 4/2002 | Kurozumi et al. |
| 2005/0002030 | A1 | 1/2005 | Kolp et al. |
| 2005/0046849 | A1 | 3/2005 | Cromwell et al. |
| 2005/0051466 | A1 * | 3/2005 | Carter ............... G01N 15/042 210/512.1 |
| 2007/0091315 | A1 | 4/2007 | Brady et al. |
| 2007/0151343 | A1 | 7/2007 | Gross et al. |
| 2009/0093807 | A1 | 4/2009 | Hyde et al. |
| 2009/0153883 | A1 | 6/2009 | Shinoda |
| 2009/0190121 | A1 | 7/2009 | Hegyi et al. |
| 2009/0194702 | A1 | 8/2009 | Meyers et al. |
| 2010/0170796 | A1 | 7/2010 | Bhatia et al. |
| 2010/0284016 | A1 | 11/2010 | Teitell et al. |
| 2010/0294916 | A1 | 11/2010 | Meyers et al. |
| 2012/0004514 | A1 | 1/2012 | Marugame |
| 2012/0122084 | A1 | 5/2012 | Wagner et al. |
| 2012/0128264 | A1 | 5/2012 | Yazdanfar et al. |
| 2013/0155499 | A1 | 6/2013 | Dixon et al. |
| 2013/0200277 | A1 | 8/2013 | Li et al. |
| 2013/0204538 | A1 | 8/2013 | Rich |
| 2014/0073000 | A1 | 3/2014 | Sun et al. |
| 2014/0098359 | A1 | 4/2014 | Gross et al. |
| 2014/0152801 | A1 * | 6/2014 | Fine ............... H04N 7/18 348/79 |
| 2014/0236494 | A1 | 8/2014 | Kolandaivelu et al. |
| 2014/0376816 | A1 | 12/2014 | Lagae et al. |
| 2015/0268244 | A1 | 9/2015 | Cho et al. |
| 2015/0276387 | A1 | 10/2015 | Kletter et al. |
| 2015/0377783 | A1 | 12/2015 | Kumer |
| 2016/0033328 | A1 * | 2/2016 | Walters ............... G01J 3/0289 356/326 |
| 2016/0231549 | A1 * | 8/2016 | Bosworth ............ G02B 21/0032 |
| 2016/0327779 | A1 | 11/2016 | Hillman et al. |
| 2017/0227466 | A1 | 8/2017 | Lo et al. |
| 2017/0322137 | A1 * | 11/2017 | Feher ............... G01N 15/1429 |
| 2021/0003498 | A1 | 1/2021 | Ota et al. |
| 2021/0190669 | A1 | 6/2021 | Ota et al. |

FOREIGN PATENT DOCUMENTS

| | | |
|---|---|---|
| CN | 102272580 A | 12/2011 |
| CN | 102495467 A | 6/2012 |
| CN | 102890049 A | 1/2013 |
| CN | 103604737 A | 2/2014 |
| CN | 103837461 A | 6/2014 |
| CN | 103930768 A | 7/2014 |
| CN | 104136907 A | 11/2014 |
| CN | 104154878 A | 11/2014 |
| CN | 104736995 A | 6/2015 |
| CN | 105579828 A | 5/2016 |
| CN | 105651656 A | 6/2016 |
| CN | 105849275 A | 8/2016 |
| EP | 2602612 A1 | 6/2013 |
| EP | 2673618 A1 | 12/2013 |
| EP | 3264031 A1 | 1/2018 |
| EP | 3372985 A1 | 9/2018 |
| JP | S613032 A | 1/1986 |
| JP | S6279329 A | 4/1987 |
| JP | H01118747 A | 5/1989 |
| JP | H07270314 A | 10/1995 |
| JP | H07325026 A | 12/1995 |
| JP | H09311102 A | 12/1997 |
| JP | 2002116133 A | 4/2002 |
| JP | 3444509 B2 | 9/2003 |
| JP | 2006520893 A | 9/2006 |
| JP | 2008523402 A | 7/2008 |
| JP | 2009115672 A | 5/2009 |
| JP | 2009180724 A | 8/2009 |
| JP | 2009180725 A | 8/2009 |
| JP | 2010203949 A | 9/2010 |
| JP | 2013015357 A | 1/2013 |
| JP | 2013178232 A | 9/2013 |
| JP | 5534214 B2 | 6/2014 |
| JP | 2014175819 A | 9/2014 |
| WO | WO-2006103920 A1 | 10/2006 |
| WO | WO-2006127967 A2 | 11/2006 |
| WO | WO-2007067999 A2 | 6/2007 |
| WO | WO-2012086195 A1 | 6/2012 |
| WO | WO-2012144886 A1 | 10/2012 |
| WO | WO-2012147804 | 11/2012 |
| WO | WO-2014146062 A2 | 9/2014 |
| WO | WO-2016136801 A1 | 9/2016 |
| WO | WO-2017073737 A1 | 5/2017 |
| WO | WO-2019241443 A1 | 12/2019 |

OTHER PUBLICATIONS

CN201680062987.7 Office Action dated Dec. 30, 2019.
Co-pending U.S. Appl. No. 17/336,720, inventors Otasadao et al., filed on Jun. 2, 2021.
EP16755545.7 European Office Action dated Jun. 24, 2020.
EP16755545.7 Extended European Search Report dated Aug. 24, 2018.
EP16859965.2 European Search Report dated Aug. 16, 2019.
EP16859965.2 European Search Report dated May 6, 2019.
Han, et al., Imaging cells in flow cytometer using spatial-temporal transformation. Scientific Reports, Aug. 18, 2015; vol. 5, No. 1: XP055477357.
International Search Report of PCT/JP2016/055412, dated May 17, 2016.
International Search Report of PCT/JP2016/082089, dated Jan. 24, 2017.
Japanese Application No. 2017-547891 Office Action dated Oct. 6, 2020.
JP2017-547891 Japanese Office Action dated Apr. 27, 2021.
Katz, et al. Compressive ghost imaging. Appl. Phys. Lett. 95, 131110 (2009).
Li, et al., Ghost imaging for an axially moving target with an unknown constant speed, Photonics Research, 2015.08; 3(4):153-157.
Li, et al., Ghost imaging of a moving target with an unknown constant speed, Applied Physics Letters, 2014; 104:251120-1-251120-3.

(56) References Cited

OTHER PUBLICATIONS

PCT/US2019/036849 International Search Report and Written Opinion dated Sep. 19, 2019.
Shibuya, et al., Monomolecular fluorescence imaging method based on ghost imaging by using circulatory pattern (second report), 2014: 863-864.
Ugawa M, Lei C, Nozawa T, Ideguchi T, Di Carlo D, Ota S, Ozeki Y, Goda K. High-throughput optofluidic particle profiling with morphological and chemical specificity. Opt Lett. Oct. 15, 2015;40(20):4803-6. doi: 10.1364/OL.40.004803. PMID: 26469624.
U.S. Appl. No. 15/552,438 Notice of Allowance dated Jul. 17, 2020.
U.S. Appl. No. 15/552,438 Notice of Allowance dated Jun. 16, 2020.
U.S. Appl. No. 15/552,438 Office Action dated Apr. 12, 2019.
U.S. Appl. No. 15/552,438 Office Action dated Aug. 9, 2018.
U.S. Appl. No. 15/552,438 Office Action dated Nov. 12, 2019.
U.S. Appl. No. 15/771,180 Notice of Allowance dated May 17, 2021.
U.S. Appl. No. 15/771,180 Office Action dated Apr. 23, 2019.
U.S. Appl. No. 15/771,180 Office Action dated Jul. 30, 2020.
U.S. Appl. No. 15/771,180 Office Action dated Jun. 8, 2020.
U.S. Appl. No. 15/771,180 Office Action dated Nov. 13, 2019.
U.S. Appl. No. 16/936,138 Notice of Allowance dated Apr. 14, 2021.
U.S. Appl. No. 16/936,138 Notice of Allowance dated Jun. 8, 2021.
U.S. Appl. No. 16/936,138 Office Action dated Oct. 22, 2020.
Zhang, et al., Study on ghost imaging via compressive sensing for a reflected object, Optik, 2013;124:2334-2338.
EP19819019.1 Extended European Search Report dated Feb. 8, 2022.
U.S. Appl. No. 17/336,720 Office Action dated Apr. 14, 2022.
EP16859965.2 Office Action dated Jul. 18, 2022.
JP2021-159163 Japanese Office Action dated Oct. 4, 2022.
U.S. Appl. No. 17/336,720 Notice of Allowance dated Oct. 27, 2022.

\* cited by examiner

GC is identifying cells only by cytoplasm's info (green)

- Miapaca: Cytoplasm(Φ15um) = green
- MCF7: Cytoplasm(Φ15um) = green, Nucleus (non sphere)=blue
- K562: Cytoplasm(Φ10um) = green

ANALYSIS DEVICE

CROSS-REFERENCE

This application is a continuation application of U.S. Non-Provisional patent application Ser. No. 15/771,180, filed Jun. 25, 2018, now U.S. Pat. No. 11,098,275, which is a 35 USC § 371 United States national stage application of International Application No. PCT/JP2016/082089, filed Oct. 28, 2016, which claims priority to Japanese Application No. 2015-212356, filed Oct. 28, 2015 and U.S. Provisional Patent Application No. 62/372,321, filed Aug. 9, 2016, each of which is entirely incorporated herein by reference.

TECHNICAL FIELD

The present invention relates to analysis technology and an analysis device.

BACKGROUND ART

For example, a flow cytometer and a flow cytometry method using the flow cytometer are disclosed in Japanese Patent No. 5534214 (Patent Document 1).

Next generation flow cytometry is expected to be a technique that is capable of flow-cytometric analysis based on imaging and molecular spectroscopy. In conventional flow cytometer, characteristics of cells are evaluated based only on the total amount of fluorescence intensity. Next generation flow cytometry is expected to be capable of analysis based on not only fluorescence intensity but also cells' high content information including morphological images and molecular spectra. This technology dramatically increases an amount of effective information utilized for single-cell analysis and improves the quality of analysis without reducing the throughput of conventional flow cytometry. To realize it, however, there have been difficulties especially in effectively processing an enormous amount of information generated by single-cell imaging cytometry. More specifically, (1) it is difficult to effectively reconstruct, recognize, process, and utilize a tremendously large amount of multi-dimensional data of cells generated in the next generation cytometry from diverse and complex cell groups with limited human knowledge and ability. (2) In high-speed cell sorting, "image" reconstruction process and classification based on the images are very costly in terms of both time and money. (3) A large amount of ineffective information is generated through measurement and analysis because the optical imaging method cannot be optimized for each object and purpose. This limits speed, sensitivity, and accuracy of the whole system.

CITATION LIST

Patent Literature

[Patent Document 1]
Japanese Patent No. 5534214

SUMMARY OF INVENTION

Technical Problem

High speed and accurate analysis as well as classification of an object of interest is essential for flow cytometer. However, for practical application of the next generation flow cytometry, it is required to overcome the following challenges. (1) it is difficult to effectively reconstruct, recognize, process, and utilize a tremendously large amount of multi-dimensional data of cells generated in the next generation cytometry. (2) In high-speed cell sorting, "image" reconstruction process and classification based on the images are very costly in terms of both time and money. (3) A large amount of ineffective information is generated through measurement and analysis because the optical imaging method cannot be optimized for each object and purpose. This limits speed, sensitivity, and accuracy of the whole system.

Therefore, an objective of the present invention is to provide an analysis device that is capable of high speed and accurate analysis as well as classification using an optical system, and that improves the speed and accuracy of analysis and classification by effectively optimizing a light illumination region in the optical system or detection system.

Solution to Problem

Basically, the present invention is based on the following knowledge. The analysis system can perform rapid and accurate analysis and classification of an observed object based on signals such as light and electromagnetic waves from the observed object by basically performing analysis on the basis of signals such as light and electromagnetic waves from the observed object without image reconstruction. The optical system, light source system, detection system, and the techniques of analysis and classification are optimized by using machine leaning. This allows rapid and accurate analysis and classification of an object of interest.

Entrusting each important point of single-cell flow cytometry to machine learning makes it possible to intelligently measure, analyze, and classify a large amount of cell information. The above-described problems are solved by implementing (1) a cell classification method that is not biased by human's limited knowledge, (2) high-speed cell space information imaging and analysis methods in which a cell "image" is not captured or reconstructed, and (3) an optical imaging method that automatically optimizes itself for each object.

First, in (1) cell classification, optimum classification without a bias of human knowledge is performed by creating a phenotype from a large amount of cell information including cell morphology, nuclear morphology, molecular localization, and molecular information using machine learning. Alternatively, the system is capable of interactive evaluation such that humans interpret the results of classification done by machines from the viewpoint of biology/genetics and then train machines again based on the interpretation. It is also possible to improve the sensitivity to specific object of cells by educating machines.

In (2) spatial information imaging and analysis, a temporal waveform signal obtained in the process of high-speed imaging using a single-pixel detector includes compressed spatial information of the object of interest (although it cannot be recognized by the human eye). Machine learning of this one-dimensional temporal waveform data is equivalent to machine learning of a two-dimensional image. Therefore, the processing speed is dramatically improved by applying machine learning directly to a one-dimensional temporal waveform without degrading the quality of information. The present inventors have developed high-speed and high-sensitivity (fluorescence) imaging technology named dynamic ghost imaging (ghost motion imaging (GMI)) with a single-pixel detection element by using an optical structure and the motion of an object to be imaged relative to the optical structure. In GMI, spatial information is compressed into a temporal waveform. By directly performing machine learning on the temporal waveform that includes spatial information, high-accuracy and high-sensitivity cell analysis equivalent to the analysis of reconstructed images can be performed without reconstructing cell space information as an "image,". This allows significant quickening of analysis and classification. Cell classification using machine learning of a GMI temporal waveform also becomes a solution for (1) because it is possible to obtain the same result as cell classification by machine learning of a GMI reconstructed image.

In (3) optimization of the optical imaging method according to each object, for example, by performing machine learning between a GMI image and the conventional camera image, for example, by dynamically correcting the optical structure used by GMI, high-speed, high-sensitivity, and high-accuracy image cytometry can be implemented. Also, it is possible to implement high-sensitivity cytometry by feeding back the cytometry result and evaluation to the optical imaging method.

A first aspect of the present invention relates to an analysis device. This analysis device includes a light source 1; a light irradiation region 3 irradiated with light from the light source 1; a light-receiving unit 7 configured to receive scattered light (including Raman scattering), transmitted light, fluorescence, or electromagnetic waves from an observed object 5 located in the light irradiation region 3 and to convert the received light or electromagnetic waves into an electrical signal; a storage unit 9 configured to receive and record the electrical signal from the light-receiving unit 7; an analysis unit 11 configured to analyze the electrical signal related to the scattered light, the transmitted light, the fluorescence, or the electromagnetic waves recorded by the storage unit 9 and record an analysis result; and an optical system control unit 13 configured to optimize the light source 1 or the light irradiation region 3 on the basis of the analysis result.

The analysis device preferably optimizes a classification algorithm of the analysis unit 11 using machine learning.

Preferably, in the analysis device, the analysis unit 11 analyzes the observed object from the electrical signal related to the scattered light, the transmitted light, the fluorescence, or the electromagnetic waves without reconstructing an image of the observed object.

In this analysis device, preferably, the optical system control unit 13 optimizes the light source 1 using the machine learning.

In this analysis device, preferably, the light from the light source 1 has a plurality of light regions 21 and the optical system control unit 13 controls an optical structure of the plurality of light regions 21.

In the analysis device, preferably, the optical system control unit 13 analyzes the region in which the observed object 3 may be present on the basis of the electrical signal and performs control so that the light irradiation region 3 is limited.

In the analysis device, preferably, the optical system control unit 13 analyzes a density of the observed object 5 on the basis of the electrical signal to obtain coarseness/fineness information of the observed object and controls the light source 1 or the light irradiation region 3 on the basis of the coarseness/fineness information.

This analysis device preferably further includes a light-receiving system control unit 27 configured to receive an electrical signal from the light-receiving unit 7 and optimize a light-receiving region 25 which is a region irradiated with light for the light-receiving unit 7. In this analysis device, preferably, the light-receiving system control unit 27 optimizes the light-receiving region 25 using machine learning.

A preferred usage form of this analysis device is a flow cytometer having any one of the above-described analysis devices. This flow cytometer has a flow cell 31 including the light irradiation region 3.

The flow cytometer preferably has a sorting unit 33 configured to recognize the observed object based on the analysis result of the analysis unit 11 and sort the observed object 5.

Advantageous Effects of Invention

According to the present invention, it is possible to provide an analysis device capable of improving the accuracy and speed of analysis and classification using the optical system. Also, according to the present invention, it is possible to provide an analysis device that improves the accuracy and speed of analysis and classification by rapidly optimizing an optical system such as a light irradiation region or a detection system.

DESCRIPTION OF EMBODIMENTS

Hereinafter, modes for carrying out the present invention will be described with reference to the drawings. The present invention is not limited to the embodiments described below and includes appropriately modified examples within a scope obvious to those skilled in the art.

Figure 1:
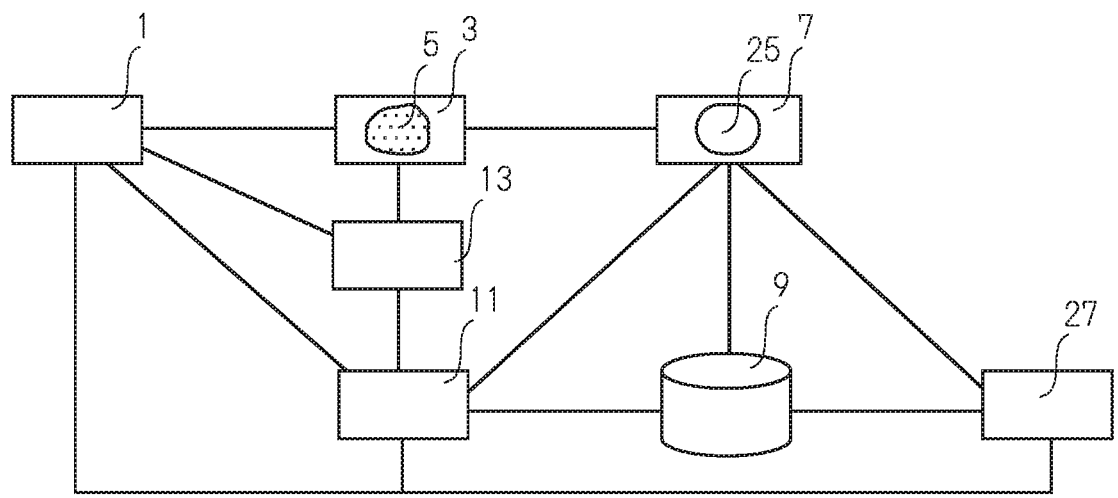
FIG. 1 is a conceptual diagram showing an outline of an analysis device of the present invention.

FIG. 1 shows an analysis device according to a first aspect of the present invention. As shown in FIG. 1, the analysis device includes a light source 1; a light irradiation region 3 irradiated with light from the light source 1; a light-receiving unit 7 configured to receive scattered light (including Raman scattering), transmitted light, fluorescence, or electromagnetic waves from an observed object 5 located in the light irradiation region 3 and convert the received light or electromagnetic waves into an electrical signal; a storage unit 9 configured to receive and record the electrical signal from the light-receiving unit 7; an analysis unit 11 configured to analyze the electrical signal related to the scattered light, the transmitted light, the fluorescence, or the electromagnetic waves recorded by the storage unit 9 and record an analysis result; and an optical system control unit 13 configured to optimize the light irradiation region 3 using machine learning or the like on the basis of the analysis result.

The analysis device preferably further includes a light-receiving system control unit 27 configured to receive the electrical signal from the light-receiving unit 7 and optimize a light-receiving region 25 which is a region where light is radiated to the light-receiving unit 7. In this analysis device, preferably, the light-receiving system control unit 27 optimizes the light-receiving region 25 using machine learning. Also, the analysis device can rapidly and accurately perform analysis even when the optical system control unit 13 is not present and only the light-receiving system control unit 27 is provided. Such an analysis device includes the light source 1; the light irradiation region 3 irradiated with light from the light source 1; the light-receiving unit 7 configured to receive scattered light, transmitted light, fluorescence, or electromagnetic waves from the observed object 5 located in the light irradiation region 3 and convert the received light or electromagnetic waves into an electrical signal; the storage unit 9 configured to receive and record the electrical signal from the light-receiving unit 7; the analysis unit 11 configured to analyze the electrical signal related to the scattered light, the transmitted light, the fluorescence, or the electromagnetic waves recorded by the storage unit 9 and record an analysis result; and the optical system control unit 27 configured to receive the electrical signal from the light-receiving unit 7 and to optimize the light-receiving region 25 which is a region where light is radiated to the light-receiving unit 7.

The outline of the present invention will be described below.

High-Accuracy and High-Sensitivity Cell Classification Method not Biased by Human Knowledge By creating a phenotype from a large amount of cell information including cell morphology, nuclear morphology, molecular localization, and molecular information generated by advanced optical technology using machine learning, objective and accurate optimum cell classification which as much as possible does not include a human knowledge bias is performed. It is also possible to analyze classification results of the machines from the viewpoint of humans and biology/genetics and interactively evaluate the classification results of the machines by educating the machines and the like. It is also possible to improve the sensitivity to specific object cells by educating the machines.

Figure 2:
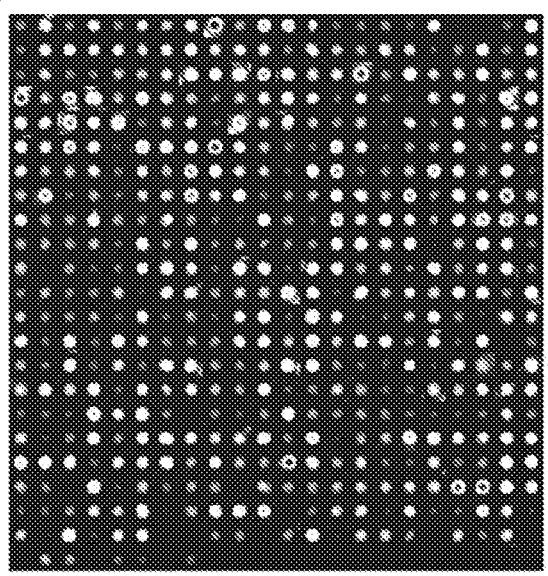
FIG. 2 is a drawing of a captured image showing results obtained by classifying GMI temporal signals generated from single cell images, using machine learning.
Figure 2:
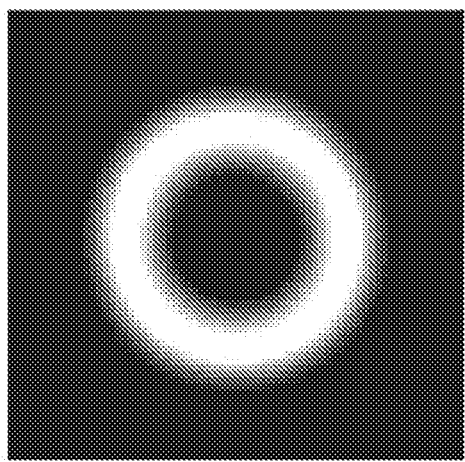

FIG. 2 shows a result of classifying GMI temporal single-cell signals generated from single-cell images using machine learning. For example, a group of GMI temporal cell signals generated by a single-cell group in a large number of complex samples (for example, blood) is first classified using unsupervised machine learning (a cell image group classified as the same type on the left of FIG. 2)) and a typical representative example of each group (a template image on the right of FIG. 2) is presented to the human. On the basis of the templates, the human selects cells according to a purpose (education for a machine). On the basis of a selection result, the machine can correct a determination criterion and classify object cells with higher sensitivity and higher speed.

Figure 3:
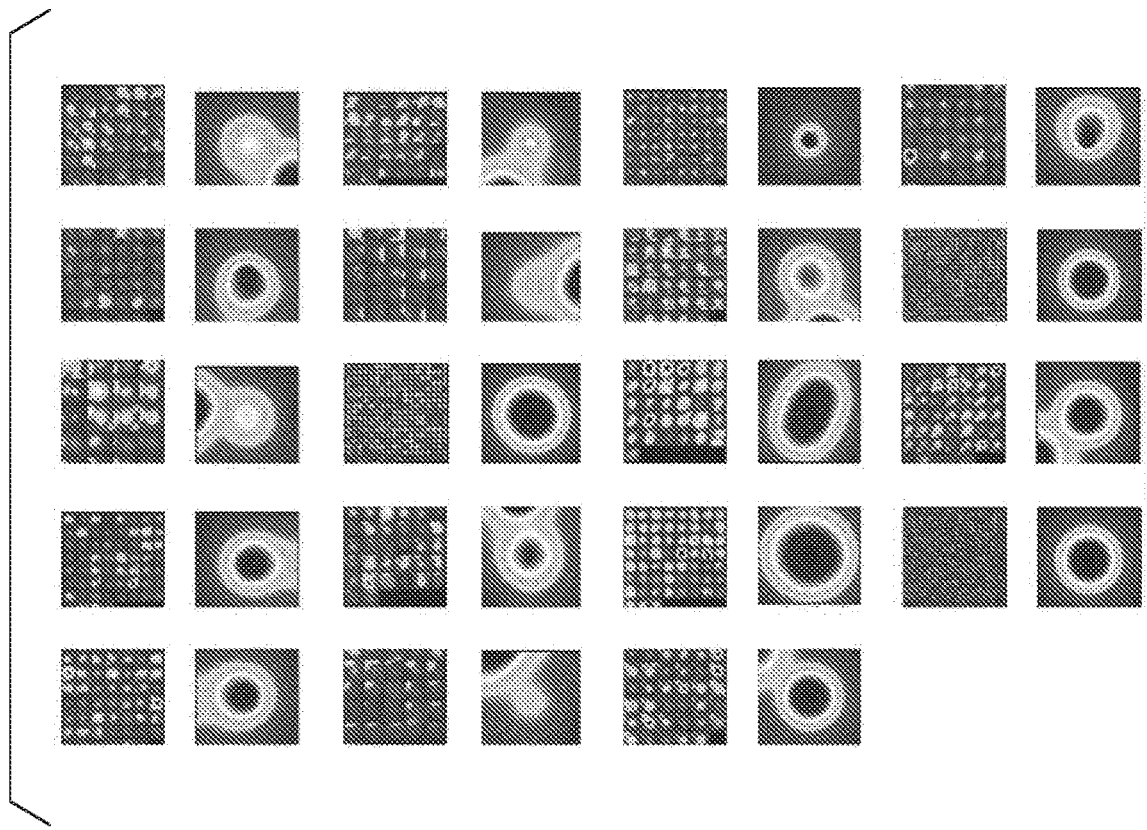
FIG. 3 is a drawing of a captured image showing results obtained by classifying GMI temporal signals generated from single cell images, using machine learning.

FIG. 3 shows a result of classifying GMI temporal single-cell signals generated from single-cell images using to machine learning. Because they are randomly captured images, a case in which the cell is not necessarily a single cell is also included. In each group, the left image shows the original cell image of the GMI temporal single-cell signals belonging to the same classification, and the right image shows a representative template cell image in the same classification generated in a GMI reconstruction process from an average signal of the GMI temporal single-cell signals belonging to the same classification. Considering application to flow cytometry, it is also possible to classify a single cell or a plurality of cells and provide an effective approach for reducing a false positive rate. For example, in current flow cytometry in which cells are classified by measuring the total number of fluorescence molecules, a main false positive result indicates a single cell, a plurality of cells, incorporated foreign matter, or the like. The present invention can assign additional spatial information to existing flow cytometry information and reduce the false positive rate. Also, generation of a representative template image in the same classification is useful for practical use because it is possible to confirm whether or not classification based on the machine learning conforms to a user's intention.

Introduction of the above-described machine learning can be applied not only to the integration of flow cytometry technology and high-speed imaging technology such as GMI, but also to the integration of flow cytometry technology and nonlinear molecular spectroscopy technology (Raman spectroscopy, stimulated Raman scattering spectroscopy, or coherent anti-Stokes Raman scattering spectroscopy). In this case, machine learning of a temporal signal of a scattered spectrum other than an image or a temporal waveform is performed, an analysis time is significantly shortened without involving a Fourier transform, and classification is performed without a human knowledge bias. It is also possible to construct an interactive system. For example, cells are classified using unsupervised machine learning, template spectra are generated, the human performs education while viewing a template, and cell classification can be performed according to a purpose with higher accuracy on the basis of supervised machine learning. High-Speed Imaging and Analysis Method of Obtaining Cell Space Information without Capturing Cell "Image"

Figure 4:
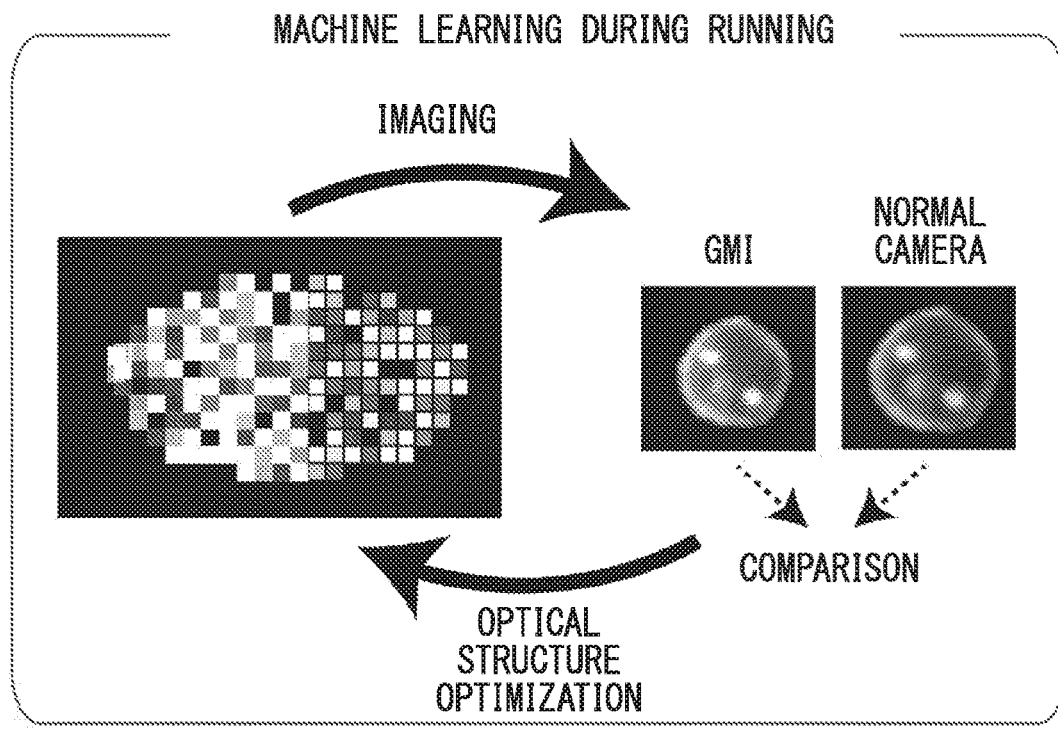
FIG. 4 is a diagram showing an example in which classification accuracy and image accuracy are improved through optimization of an optical structure by comparing a reconstructed GMI image of the observed object with a normal camera image.

For example, space information of an imaging object (which cannot be recognized by the human eye) is effectively compressed and included in a temporal waveform signal obtained in a process of high-speed imaging technology using a single-pixel detection element in the GMI method. A process of causing the machine to learn such one-dimensional temporal waveform data is equivalent to a process of causing the machine to learn a two-dimensional image. Thus, a processing speed can be dramatically improved when no image reconstruction process is performed and the information and classification accuracy will not be degraded. It is possible to process cell space information with high speed, high accuracy, and highly sensitivity without reconstructing an "image." For example, the unsupervised cell classification shown in FIGS. 2 and 3 also uses compressed temporal waveform signals. The compressed temporal signals can be used directly without involving the image reconstruction process in highly accurate and highly sensitive cell classification released from a human bias.
Optical Imaging Method that Automatically Performs Optimization According to Object For example, machine learning is performed between a GMI image and a conventional camera image to dynamically correct an optical structure in which GMI is used. Also, it is possible to apply a cytometry result (including human recognition of whether specific information of the observed object is desired or the like) to an optical imaging method.
Introduction of Automatic Machine Learning into Optical Imaging Process As shown in FIG. 4, characteristics of the observed object differ greatly (bacteria, blood, and the like) according to a purpose or a researcher. By introducing automatic machine learning into an optical imaging process, the required optical structure is automatically optimized using a light spatial modulator or the like. There are parameters such as an overall shape (a rectangle, a rhombus, or an ellipse), a size, a density of a bright part of a random pattern, a size of each bright part of a pattern, and the like in the optical structure. Using the machine learning, this parameter group is optimized to improve accuracy while speeding up optical imaging and information processing.

By introducing machine learning for the observed object of the next generation flow cytometry for generating a large amount of multi-dimensional information, a. large-quantity/multi-dimensional data can be processed, b. fast analysis/classification processing is possible, c. high accuracy is possible, d. human individual differences, human fatigue, and the like do not intervene, and e. it is possible to accurately find characteristics of cells which could not be recognized by limited human knowledge and perception. It is possible to execute high-accuracy and high-speed analysis and classification from spectral data which cannot be recognized by the human eye not only when imaging is performed for spatial information of cells according to fluorescence imaging or the like but also in molecular spectroscopy.

Processing can be speeded up without degrading the quality of information by processing a temporal waveform signal obtained by effectively compressing cell spatial information in the optical imaging method instead of two-dimensional information of the cell image.

By optimizing the optical imaging method in accordance with the observed object, it is possible to accurately collect object information while effectively compressing the object information and it is possible to speed up optical imaging and information processing without reducing the accuracy of cytometry. Also, by applying the cytometry result (including human recognition of whether specific information of the observed object is desired or the like) to the optical imaging method, it is possible to make a modification suitable for the purpose and increase the sensitivity of the cytometry.

Each element in the analysis device of the present invention will be described below.
Optical System The light source 1 and the light irradiation region 3 irradiated with the light from the light source 1 form an optical system for irradiating the observed object with light. The optical system may appropriately include an optical element including a mirror or a lens (not shown), a spatial light modulator, and a filter. The optical system may be an optical system (a system) having a structured illumination pattern having a plurality of regions with different optical characteristics. An example of the optical system may be a group of optical elements having a light source and a filter for receiving the light from the light source and forming a structured illumination pattern. Another example of the optical system is a light source group (or a light source group and an optical element group including optical elements) having a plurality of light sources for configuring an illumination pattern.

For example, light from the light source passes through a filter having a pattern of optical characteristics and is radiated to an object to be measured with a pattern of light. The light source may be continuous light or pulsed light, but continuous light is preferable. The light source may include a single light source or may include a plurality of light sources regularly arranged (for example, the light source may include a plurality of light sources arranged at equal intervals in a vertical direction and a horizontal direction). In this case, it is preferable that one or both of the intensity and the wavelength can be controlled in the plurality of light sources.

The light source may be white light or monochromatic light. Although examples of optical characteristics are characteristics related to one or more of an intensity of light, a wavelength of light, and polarization (e.g., transmittance), the present invention is not limited thereto. An example of a structured illumination pattern having a plurality of regions having different optical characteristics includes a plurality of regions having a first intensity of light and a plurality of regions having a second intensity of light. Examples of the plurality of regions having different optical characteristics have portions with different optical characteristics randomly scattered in a certain region. Also, in another example of the plurality of regions having different optical characteristics, a plurality of regions partitioned in a lattice shape are present and the plurality of regions include at least a region having a first intensity of light and a region having a second intensity of light. For example, the structured illumination pattern having a plurality of regions having different optical characteristics can be achieved by adjusting the intensity and frequency of each light source included in the plurality of light sources and can be obtained by radiating light from the light sources to a transparent film on which a pattern is printed. Preferably, the structured illumination pattern is radiated to the observed object.

When the observed object 5 is mounted on, for example, a specific stage or moves on a specific stage, a region irradiated with light from the light source in the stage is the light irradiation region 3. Normally, the observed object 5 is located in the light irradiation region 3 or passes through the light irradiation region 3.

Various types of observed objects 5 can be designated as the observed object according to a field of application. Although examples of the observed object are cells, body fluids, and the eyeball (which may be a moving eyeball), the present invention is not limited thereto.

Light-Receiving Unit (Imaging Unit)

The light-receiving unit 7 is a detection element configured to receive scattered light (including Raman scattering), transmitted light, fluorescence, or electromagnetic waves (hereinafter also simply referred to as an "optical signal") from the observed object 5 located in the light irradiation region 3 and convert the optical signal into an electrical signal. If the electromagnetic waves are received, it is possible to perform analysis based on various types of spectroscopic technologies. For example, the light-receiving unit 7 may include an optical element such as a light spatial modulator or may be a light-receiving unit capable of appropriately adjusting an optical signal from the observed object 5. If a region where optical signals from the observed object 5 located in the light irradiation region 3 reach the light-receiving unit 7 is a light-receiving region, the light-receiving region may be controlled by these optical elements.

In other words, the light-receiving unit 7 may be a structured detection system having a plurality of regions having different optical characteristics. The light-receiving unit 7 may be configured to include a light spatial modulator or an optical element using a film partially coated or painted with a material that changes transmittance such as aluminum, silver, or lead for an optical element. In other words, the light-receiving unit 7 may be configured by arranging the above-described optical element between the observed object 5 to which the uniform illumination is radiated and the light-receiving unit 7, or the like. If a region where optical signals from the observed object 5 located in the light irradiation region 3 reach the light-receiving unit 7 is set as a light-receiving region, the light-receiving region may be controlled by these optical elements.

The light-receiving unit 7 includes a light-receiving device (an imaging device) and preferably includes one or a few pixel detection elements. Although examples of one or a few pixel detection elements are a photomultiplier tube and a multichannel plate photomultiplier tube, the present invention is not limited thereto. Because a few pixel detecting elements are compact and operable at a high speed in parallel, pixel detection elements are preferably used in the present invention. Examples of a single-pixel detection element are disclosed in Japan Patent Nos. 4679507 and 3444509. Examples of the light-receiving device include one or a few light-receiving devices such as a photomultiplier tube (PMT), a line type PMT element, an avalanche photodiode (APD), and a photodetector (PD) or a CCD camera and a CMOS sensor.

The light-receiving unit 7 may have a plurality of types of detection devices. If reconstruction of an image is required for optimization, for example, one of the detection devices may be a detection system based on GMI and another detection device may be a normal camera. In this case, as shown in FIG. 4, an image derived from the GMI and an image derived from the camera are compared and it is only necessary for an optical system or a detection system to perform adjustment so that a difference between a reconstructed image derived from the GMI and the image derived from the camera is reduced.

Storage Unit

The storage unit is an element connected to an element such as a light-receiving unit to exchange information with the connected element and configured to record the information. When the light-receiving unit includes a storage device such as a memory or a hard disk, they function as a storage unit. Also, if the light-receiving unit is connected to a computer, a server or the like connected to the computer functions as a storage unit in addition to the storage device (a memory, a hard disk, or the like) of the computer. The storage unit receives an electrical signal from the light-receiving unit 7 and records the received electrical signal.

The analysis unit recognizes and classifies electrical signals related to scattered light, transmitted light, fluorescence, or electromagnetic waves recorded by the storage unit 9 and records results of recognition and classification. Using machine learning for analysis, cell data such as GMI compressed temporal signals which cannot be read by the human eye can be recognized and classified. That is, it is preferable that the analysis unit can store a program that performs machine learning and performs the machine learning on given information. Although specific details of the recognition and classification are described in the examples, the analysis unit, for example, recognize a type of class to which the observed object belongs. For example, in the recognition using a k-means method, a class in which a distance between an electrical signal pattern serving as a template of each class obtained in advance and a newly obtained electrical signal pattern is minimized is designated as a class of a newly obtained electrical signal pattern. Moreover, electrical signals to be observed are stored, and a pattern group of stored electrical signals is classified. In this classification, classification is performed so that each electrical signal pattern from an average electrical signal pattern of each class is minimized. Also, a new electrical signal pattern is classified on the basis of this stored data and classification data. Further, if necessary, the stored data and classification data are updated on the basis of a new electrical signal pattern. Updating the classification data indicates that a new electrical signal pattern is used to calculate average data and intermediate value data of each class. For example, the classification data is updated by adding a new electrical signal pattern c to (a+b)/2 which is an average value of electrical signal patterns a and b and obtaining (a+b+c)/3.

The analysis unit may include, for example, a temporal signal information acquisition unit configured to receive an optical signal during a fixed period and acquire temporal signal information of the optical signal and a partial signal separation unit configured to separate partial temporal signal information in a partial region of an observed object from the temporal signal information. For example, if temporal signal information when the observed object is a contaminant which is not a cell or the like is stored and partial temporal signal information of a certain observation part is classified as a pattern classified as partial temporal signal information of a contaminant or the like which is not a cell, it is possible to ascertain that there is no cell in the observation part. Because it is possible to ascertain a region where there is no cell without reconstructing an image, the speed of processing is increased, control is performed so that no light is radiated to part thereof as will be described below or temporal signal information is not adopted thereafter, and therefore, it is possible to reduce an amount of information, reduce the number of errors, and speed up processing. According to a field of application, the analysis unit may further include a partial image reconstruction unit configured to extract or reconstruct information about an image of each part of the observed object (an intensity of emitted light or the like) from the obtained partial temporal signal information of the observed object. Also, the analysis unit may include an image reconstruction unit for reconstructing an image related to the observed object using an image of each part of the observed object reconstructed by the partial image reconstruction unit. Although this case is preferable because the human can perform a verification operation, analysis and classification becomes time-consuming because the image of the observed object is reconstructed once.

A detected signal includes information of the detected intensity for each change over time. The temporal signal information acquisition unit acquires temporal signal information of an optical signal. In an example of the temporal signal information acquisition unit, the light-receiving unit of one or a few pixel detection elements receives the detected signal received, detected, and stored for a fixed time as the temporal signal information. The temporal signal information acquired by the temporal signal information acquisition unit may be appropriately stored in the storage unit. Also, the temporal signal information acquired by the temporal signal information acquisition unit may be sent to the partial signal separation unit so that the temporal signal information is used in an arithmetic process of the partial signal separation unit.

The partial signal separation unit is an element for separating the partial temporal signal information in the partial region of the observed object from the temporal signal information. The temporal signal information includes a detected signal derived from each part of the observed object. Thus, the partial signal separation unit separates partial temporal signal information which is temporal signal information in each partial region of the observed object from the temporal signal information. At this time, the partial signal separation unit reads information H about the stored illumination pattern and separates the partial temporal signal information using the information H about the read illumination pattern and the temporal signal information. That is, because there is a change corresponding to the information H about the illumination pattern, the temporal signal information can be separated into the partial temporal signal information using the information H about the illumination pattern. The partial temporal signal information which is temporal signal information in each partial region of the observed object from the temporal signal information may be appropriately stored in the storage unit. Also, according to a field of application, the partial temporal signal information may be sent to the partial image reconstruction unit for an arithmetic process of the partial image reconstruction unit.

The partial image reconstruction unit is an element for extracting or reconstructing information about an image of each part of the observed object (the intensity of emitted light or the like) from the partial temporal signal information. Because the partial temporal signal information is temporal signal information in each partial region, information f about an intensity of light in each region can be obtained. The information about the image of each part of the observed object (the intensity of emitted light or the like) may be appropriately stored in the storage unit. Also, the information about the image of each part of the observed object (the intensity of emitted light or the like) may be sent to the image reconstruction unit for the arithmetic process of the image reconstruction unit. In this case, for example, because the observed object can be analyzed before the image is reconstructed, it is possible to optimize the light source system and the detection system rapidly and also obtain the image of the observed object.

The image reconstruction unit is an element for reconstructing an image related to an observed object using images of parts of the observed object reconstructed by the partial image reconstruction unit. Because the image of each part of the observed object is an image of each region of the observed object, the image related to the observed object can be reconstructed by adjusting the image.

The analysis device preferably optimizes a classification algorithm of the analysis unit 11 using machine learning. That is, the analysis unit 11 includes a classification algorithm for performing various types of analysis. This classification algorithm is optimized using machine learning. The classification algorithm includes an algorithm for making a classification using the classification of the observed object described above or the classification of a signal when the observed object is not present. An example of the analysis is a process of ascertaining a characteristic optical signal component of the observed object, setting a threshold value to be used in a classification operation, or setting a condition for optimizing the optical system and the detection system.

The machine learning is well-known as disclosed in, for example, Japanese Patent No. 5574407, Japanese Patent No. 5464244, and Japanese Patent No. 5418386. An example of the machine learning is learning using an Ada Boosting algorithm. For example, the machine learning may be a process of obtaining optical signals of a plurality of objects among observed objects and learning characteristics of the observed object from the obtained optical signals. By performing machine learning, it becomes possible to detect the presence or absence of specific cells extremely efficiently and rapidly. The object of the machine learning is not limited to an image, for example, it being only necessary to detect a vibration that is not imaged as in a case in which Raman spectroscopy is used and to use a detected signal for an analysis object. For example, the analysis unit can analyze optical signals of a plurality of observed objects using the machine learning of and perform analysis such as the classification/recognition of the optical signals of the observed objects.

In this analysis device, preferably, the analysis unit 11 analyzes an observed object without reconstructing an image of the observed object with an electrical signal related to scattered light, transmitted light, fluorescence or electromagnetic waves. For example, the analysis unit 11 analyzes the observed object using the above-described temporal signal information, partial temporal signal information, or GMI. In this example, it is possible to analyze whether or not an observed object is a specific object and analyze information about the observation target including a size and a position of the observation target by recognizing a pattern or the like using machine learning for a plurality of objects and collating the temporal signal information, the partial temporal signal information, or the GMI with the pattern or the like.

Optical System Control Unit

The optical system control unit 13 is an element for optimizing the light source 1 or the light irradiation region 3 on the basis of an analysis result.

A control signal (a control command) for controlling the light-receiving unit 7, the light source 1, or the optical element constituting the optical system may be requested in the analysis unit described above, or may be requested in the optical system control unit 13. If the control command is requested in the analysis unit, the optical system control unit 13 can optimize a light source system by controlling the light source 1 or the optical element constituting the optical system in accordance with the control signal (the control command) requested by the analysis unit 3.

An example of the optical system control unit 13 is a computer connected so that information can be exchanged with a control unit configured to control the light-receiving unit 7, the light source 1, or the optical element constituting the optical system. In this computer, a program is installed so that a specific arithmetic process and an input/output can be performed. An example of this program is a program for performing machine learning.

In an image capturing mechanism such as GMI, it is preferable that the optical system control unit 13 perform processing with the temporal waveform electrical signal (GMI) as it is without reconstructing the image of the observed object on the basis of the electrical signal from the light-receiving unit 7. According to a field of application, a function of reconstructing the image of the observed object may be provided. In this case, the image quality can be verified.

In the spectrum temporal waveform recording mechanism such as Raman spectroscopic measurement, it is preferable that the optical system control unit 13 process the temporal waveform electrical signal as it is without performing a Fourier transform on the spectrum and analyzing a molecular spectrum in the frequency domain on the basis of the electrical signal from the light-receiving unit 7. However, according to a field of application, the optical system control unit 13 may analyze the molecular spectrum in the frequency domain by performing a Fourier transform on an electromagnetic wave spectrum.

In this analysis device, preferably, the optical system control unit 13 optimizes the light source 1 or the light irradiation region 3 using machine learning. An example of optimization of the light source 1 is to adjust an intensity of light of the light source 1. In this analysis device, preferably, the light from the light source 1 has a plurality of light regions 21, and the optical system control unit 13 controls an optical structure of the plurality of light regions 21. In this analysis device, preferably, the optical system control unit 13 analyzes a region of presence of the observed object 5 on the basis of the electrical signal and performs control for limiting the light irradiation region 3.

In this analysis device, preferably, the optical system control unit 13 analyzes a density of the observed object 5 on the basis of the electrical signal to obtain coarseness/fineness information of the observed object and controls the light source 1 or the light irradiation region 3 on the basis of the coarseness/fineness information.

Light-Receiving System Control Unit

The analysis device preferably further includes the light-receiving system control unit 27 configured to receive an electrical signal from the light-receiving unit 7 and optimize the light-receiving region 25 which is a region where light is radiated to the light-receiving unit 7. In the light-receiving system control unit 27, the analysis unit described above may perform analysis of the light-receiving system. That is, for example, the analysis unit adopts a program for machine learning, and classifies a received optical signal of part of the light-receiving unit where no useful information is obtained. If the received optical signal of a certain part of the light-receiving unit is classified as this classification, for example, processing is performed so that information from this part is not used for analysis. Accordingly, it is possible to reduce the throughput of the analysis and to perform the process rapidly. In the analysis device, preferably, the light-receiving system control unit 27 optimizes the light-receiving region 25 using machine learning. In this preferred form, the light source 1 or the light-receiving region 25 may be optimized using a technique similar to optimization of the optical system by the optical system control unit 13. An example of the light-receiving system control unit 25 is a computer connected so that information can be exchanged with the control device configured to control the light-receiving unit 7, the light source 1, or the optical elements constituting the light-receiving system and the light-receiving region 25. That is, the present description discloses optimization of the optical system and optimization of the light-receiving system and discloses optimization of only the light-receiving system.

The analysis device may include various types of element in a well-known analysis device. An example of such an element is a relative position control mechanism.

Next, an operation example of the imaging device of the present invention will be described.

Figure 5:
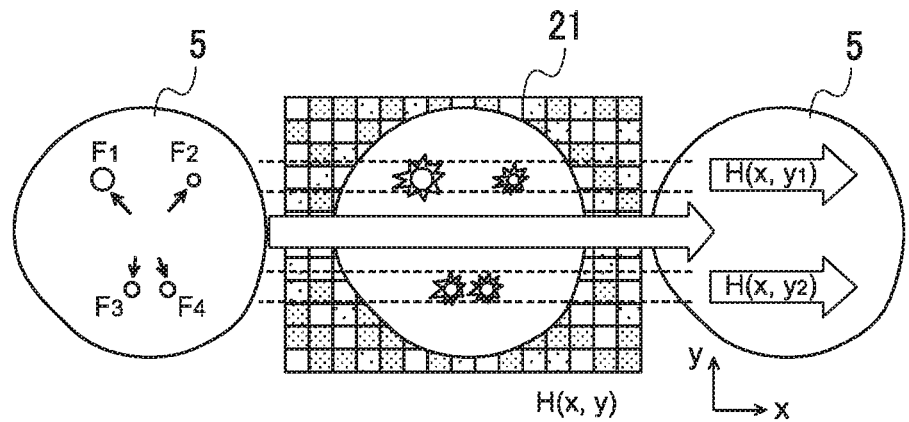
FIG. 5 is a conceptual diagram showing that an observed object passes through a patterned illumination.

FIG. 5 is a conceptual diagram showing that the observed object passes through patterned illumination. As shown in FIG. 5, the observed object 5 is moved by a relative position control mechanism and passes through patterned illumination of the optical system. This patterned illumination optical structure exhibits its intensity distribution in a matrix of $H(x, y)$. This observed object 5 has fluorescence molecules indicated by optical spatial information, for example, $F_1$ to $F_4$. These fluorescence molecules do not emit fluorescence according to an intensity of received light or an intensity of emitted fluorescence varies. That is, in this example, the fluorescence molecule denoted by $F_2$ first emits fluorescence and an intensity of emitted fluorescence is affected by the patterned illumination through which the observed object 5 passes. The light from the observed object 5 may be appropriately focused according to a lens or the like. Then, the light from the observed object 5 is transmitted to one or a few pixel detection elements. In the example of FIG. 5, a traveling direction of the observed object is set as an x-axis, and a y-axis is provided in a direction perpendicular to the x-axis which is in the same plane as that of the x-axis. In this example, $F_1$ and $F_2$ are observed as fluorescence on $y_1$ which is the same y coordinate ($F_1$ and $F_2$ are denoted by $H(x, y_1)$. Also, $F_3$ and $F_4$ are observed as fluorescence on $y_2$ which is the same y coordinate ($F_3$ and $F_4$ are denoted by $H(x, y_2)$).

Figure 6:
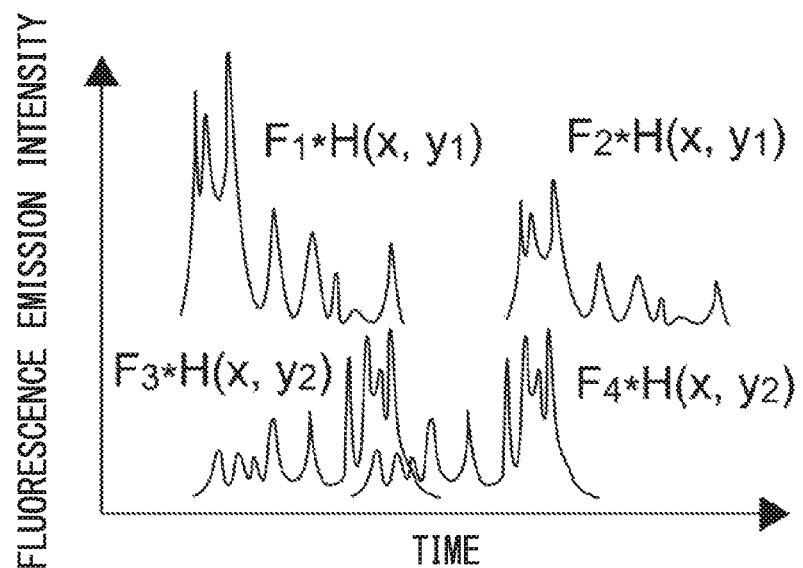
FIG. 6 is a conceptual diagram showing a state of fluorescence emitted by an observed object shown in FIG. 5.

FIG. 6 is a conceptual diagram showing a state of fluorescence emitted by the observed object shown in FIG. 5. As shown in FIG. 6, the fluorescence is emitted from each fluorescence molecule. For example, because $F_1$ and $F_2$ experience the same illumination pattern, they are considered to have similar time response patterns or output patterns. On the other hand, the intensity of emitted light is considered to be different between $F_1$ and $F_2$. Thus, intensities of emitted light of $F_1$ and $F_2$ can be approximated so that they are products of $F_1$ and $F_2$ which are coefficients specific to each light emitting molecule and $H(x, y_1)$ which is a time response pattern common to the coordinate $y_1$. The same is true for $F_3$ and $F_4$.

Figure 7:
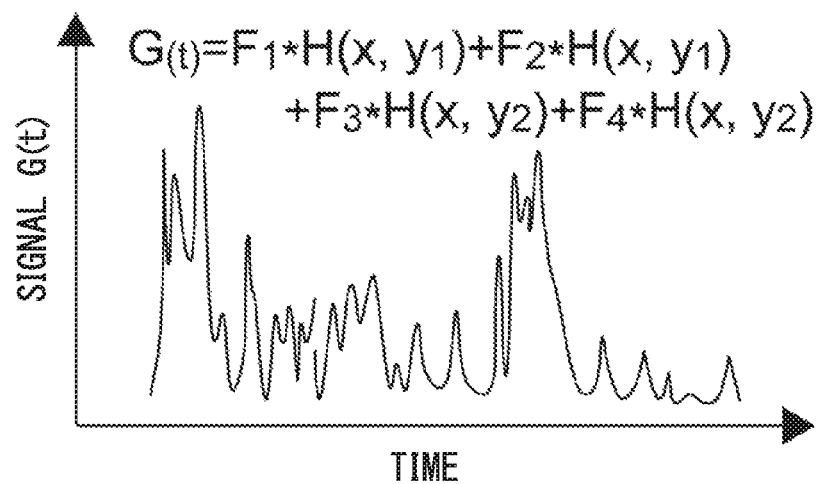
FIG. 7 is a conceptual diagram showing a temporally detected signal when fluorescence emitted by the observed object shown in FIG. 5 is detected.

FIG. 7 is a conceptual diagram showing a detected signal when fluorescence emitted by the observed object shown in FIG. 5 is detected. This detected signal is observed as a sum signal of fluorescence signals shown in FIG. 6. Then, this signal includes a time-varying pattern $H(x, y_n)$ of a plurality of intensities. Then, it is possible to obtain each coordinate and a fluorescence coefficient (an intensity of fluorescence) at each coordinate from each intensity ($G(t)$) of the detected signal and $H(x, y_n)$.

Figure 8:
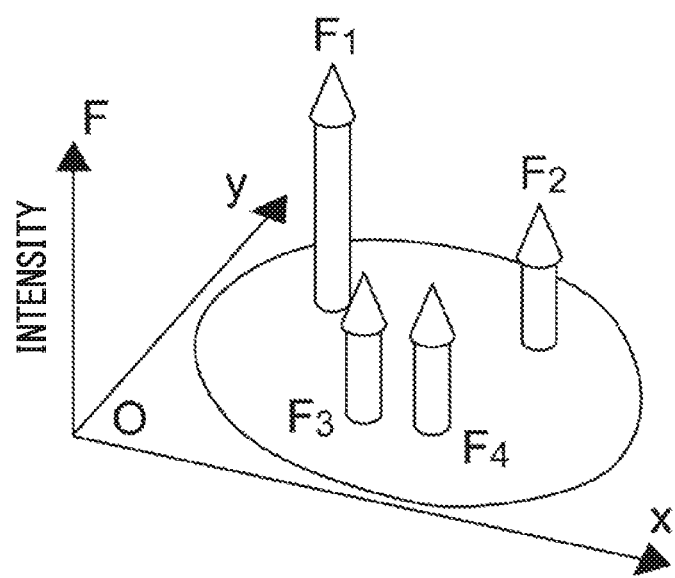
FIG. 8 is a conceptual diagram showing the position of a fluorescence molecule obtained from the intensity of a detected signal and the intensity of fluorescence, i.e., a fluorescence image.

FIG. 8 is a conceptual diagram showing a position and an intensity of fluorescence of fluorescence molecules obtained from an intensity of a detected signal. As shown in FIG. 8, fluorescence coefficients (intensities of fluorescence) $F_1$ to $F_4$ can be obtained from the detected signal $G(t)$.

Figure 9:
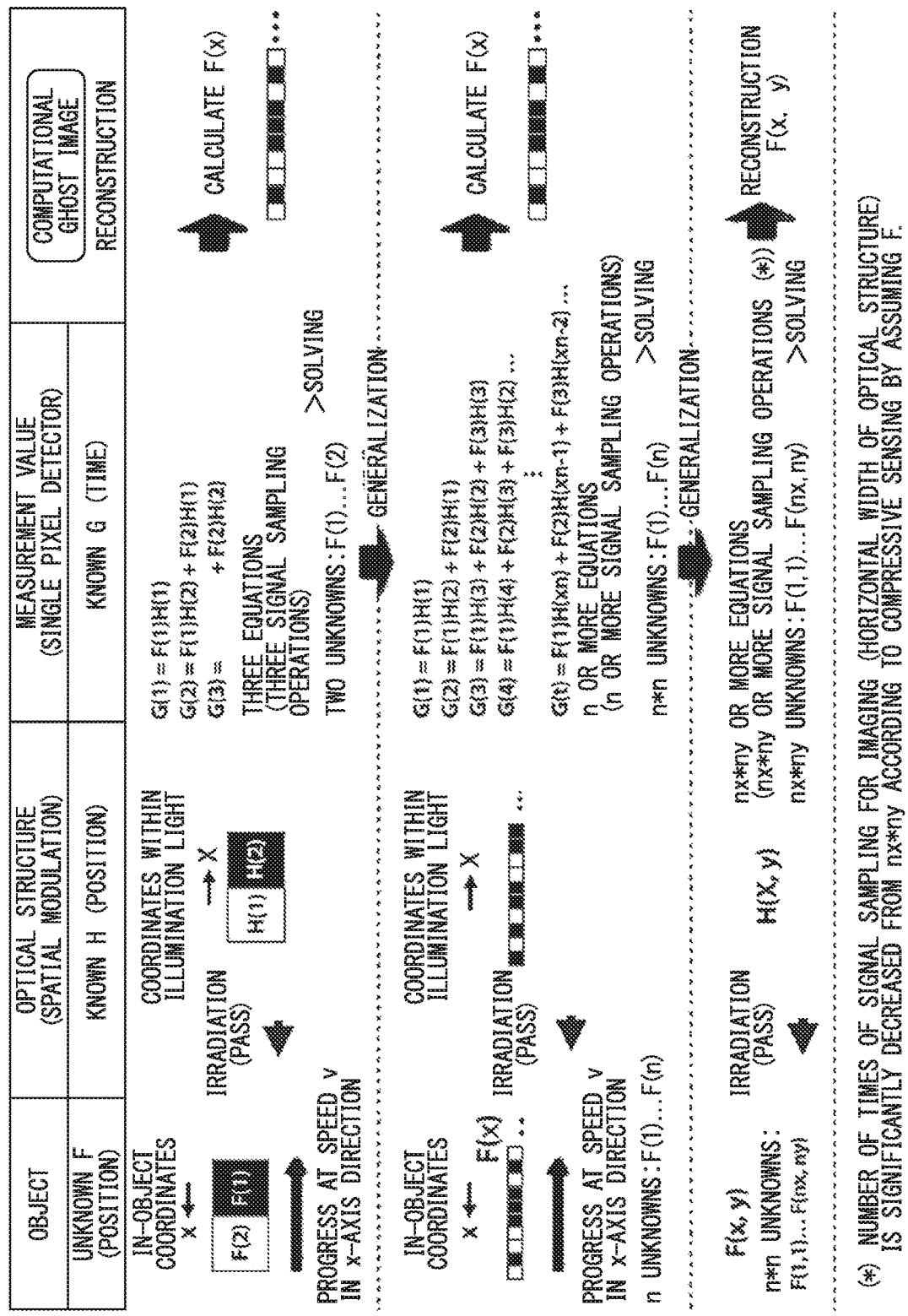
FIG. 9 is a diagram showing a principle of image reconstruction.

The above-described principle will be described in more detail. FIG. 9 is a diagram showing the principle of image reconstruction. For example, $F(1)$ and $F(2)$ are assumed to be in-object coordinates. Then, at time 1, light of a first pattern is radiated to $F(1)$ and is not radiated to $F(2)$. At time 2, light of a second pattern is irradiated to $F(1)$ and light of the first pattern is radiated to $F(2)$. At time 3, no light is radiated to $F(1)$ and the light of the second pattern is radiated to $F(2)$. Then, the detected signal $G(t)$ is as follows. $G(1)=F(1)H(1)$, $G(2)=F(1)H(2)+F(2)H(1)$, and $G(3)=F(2)H(2)$. When the above is solved, $F(1)$ and $F(2)$ can be analyzed. Using this principle, the coordinates $F(1)$ to $F(n)$ can be obtained by performing analysis in a similar manner even if there are more in-object coordinates.

Next, if the object is two-dimensional, internal coordinates of the observed object are assumed to be $F(x, y)$. On the other hand, pattern illumination is also assumed to have coordinates. Assuming that there are n internal coordinates of the observed object in the x-axis direction and n in the y-axis direction, the number of unknowns of $F(x, y)$ is n×n. $F(x, y)$ ($0 \leq x \leq n$ and $0 \leq y \leq n$) can be reconstructed by measuring the signal in the same manner as above and analyzing the obtained signal $G(t)$.

Figure 10:
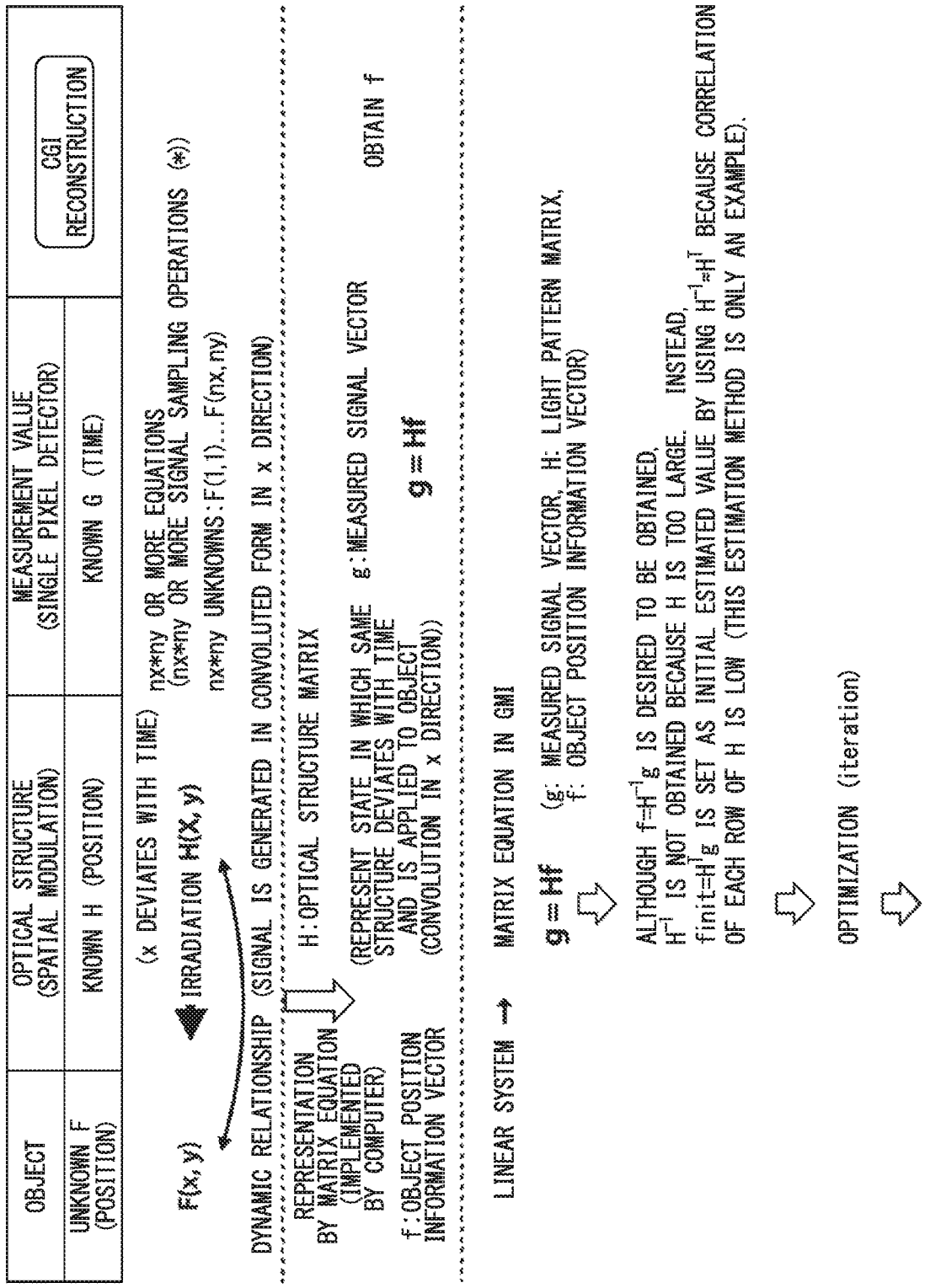
FIG. 10 is a diagram showing an example of an image reconstruction process.

FIG. 10 is a diagram showing an example of the image reconstruction process. In this example, the image is represented as f (an object position information vector) in a matrix equation. Then, patterned illumination is represented by $H(X, y)$, and X is represented by a variable which varies with time. Also, an intensity of a detected signal is represented as g (a measured signal vector). Then, these can be represented as g=Hf. As shown in FIG. 10, it only necessary to multiply an inverse matrix $H^{-1}$ of H from the left in order to obtain f. On the other hand, H may be too large to easily obtain the inverse matrix $H^{-1}$ of H. In this case, for example, a transposed matrix $H^t$ of H may be used instead of an inverse matrix. Using this relationship, it is possible to obtain an initial estimated value $f_{int}$ off. Thereafter, by optimizing f with the initial estimated value $f_{int}$ off, the image of the observed object can be reconstructed.

In other words, FIG. 10 is a diagram showing an example of the image reconstruction process. In this example, the image is represented as f (an object position information vector) in a matrix equation. Then, the patterned illumination is represented as $H(X, y)$, and X is represented by a variable which varies with time. Also, an intensity of a detected signal is represented as g (a measured signal vector). Then, these can be represented as g=Hf. As shown in FIG. 10, it only necessary to multiply the inverse matrix $H^{-1}$ of H from the left in order to obtain f. On the other hand, H may be too large to easily obtain the inverse matrix $H^{-1}$ of H. In this case, for example, an initial estimated value $f_{init}$ off can be obtained as a result of multiplying a transposed matrix $H^T$ of H by g. Thereafter, it is possible to reconstruct the image of the observed object by optimizing f with the initial estimated value $f_{init}$ off.

Shape of Optical Structure Adjusted to Shape of Observed Object

Observed objects in cytometry such as cells are spherical in many cases. At this time, the overall shape of the optical structure need not be rectangular. For example, bright parts at the four corners of an optical structure are changed to dark parts and the dark parts enlarged to an extent at which the quality does not deteriorate. If the quality drops, it is only necessary to repeat a cycle in which a few new points are added to the four corners.

During cell imaging, a dense structure of cytoplasm, nuclei, or the like and a sparse structure of a cell membrane, localized molecules, or a specific chromosome label (a FISH method or the like) exist. Basically, in GMI, a sparse optical structure is desirable for a dense object structure, and it is desirable to design a dense optical structure for a sparse object structure. First, the density of the object is recognized on the basis of the GMI electrical signal. For example, when a ratio of a value of an object signal integrated over time to a product of a maximum value of the object signal and a time width of the object signal (a product of a value of the object signal integrated over time/a maximum value of the object signal and a time width of the object signal) is greater than or equal to a fixed value, the object is dense. Also, when the ratio is less than or equal to the fixed value, the object is sparse. This value is adjusted according to a sample or an object structure.

On the basis of this recognition, a more sparse or dense optical structure is designed. For example, the occupancy of a random bright part relative to the whole structure is increased or decreased and a new random pattern is created (the current GMI optical structure uses a DMD/optical mask and the structure is simply random; thus, two values of brightness and darkness are present and a bright part is specified as any % of the whole and randomly scattered). Finally, the above-described cycle is repeated until the above-described ratio (the ratio of the value of the object signal integrated over time to the product of the maximum value of the object signal and the time width of the object signal) falls in a certain fixed range (depending upon the object).

Intensity of S/N of Object Signal

According to the object, an intensity of an optical signal is very weak and an S/N ratio is low. If the S/N ratio is low, highly accurate cell information processing and cytometry may not be able to performed.

One technique for increasing the S/N ratio in GMI is to perform a plurality of binning operations on pixels in a spatial light modulator and set the pixels subjected to the binning operations as unit pixels of the GMI optical structure. Thereby, an intensity of light of the unit pixel of the GMI optical structure can be increased and the S/N can be improved.

Also, in Raman spectroscopy, one technique for increasing the S/N ratio is to reduce light radiation to a part which does not pass through the object. Thereby, the intensity of noise light can be reduced and S/N can be improved.

A simplest binning technique is a method of binning the same number of pixels in vertical and horizontal directions such as 2*2 and 3*3. However, this increases the structural size of the spatial modulator (corresponding to the real size of the GMI optical structure on the sample), and the throughput, an amount of information, and the quality deteriorate.

Binning is done in a horizontally elongated rectangle, for example, 1 pixel in length*2 pixels in width. Then, because the spatial resolution in the GMI is determined by the size of the vertical pixels, the spatial resolution does not deteriorate. However, the number of horizontal pixels (corresponding to an actual horizontal width of the GMI optical structure on the sample) of the spatial modulator becomes large and the throughput is sacrificed.

Binning is done in a vertical rectangle, 2 pixels in length*1 pixel in width. Then, because the spatial resolution in the GMI is determined according to a size of the vertical pixels, the spatial resolution deteriorates. However, the number of horizontal pixels (corresponding to the actual horizontal width of the GMI optical structure on the sample) of the spatial modulator does not change and the throughput does not deteriorate.

During cell imaging, a complex structure such as a cytoskeletal structure, a virus infection path, or a cell signal network is provided. It is difficult to design an optimum optical structure for such a complex structure. At this time, on the basis of the GMI electrical signal, the optical structure can be automatically optimized using machine learning, for example, for the purpose of improving the quality of the reconstructed image. Also, in optimization of the optical structure using machine learning, optimization including the above-described example can be achieved, for example, by setting an objective function to improvement of the imaging throughput, reduction of an amount of calculation for the electrical signal, reduction of an amount of image information, improvement of the image quality, improvement of sensitivity to a target feature quantity (a nucleus/cytoplasm ratio, a cell size, a chromosome aggregation image, the number of chromosomes, or the like), improvement of S/N of a signal, improvement of recognition accuracy, or the like.

For example, during cell imaging based on GMI, the optical structure can be optimized with a well-known machine learning and optimization algorithm. Well-known machine learning and optimization algorithms include evolutionary algorithms and simulated annealing. For example, it is possible to achieve the above-described objective and optimize an optical structure using machine learning by setting minimization of an area of the illumination region, maximization of image quality or recognition accuracy, maximization of S/N, or the like as an objective function of the optimization algorithm.

Figure 11:
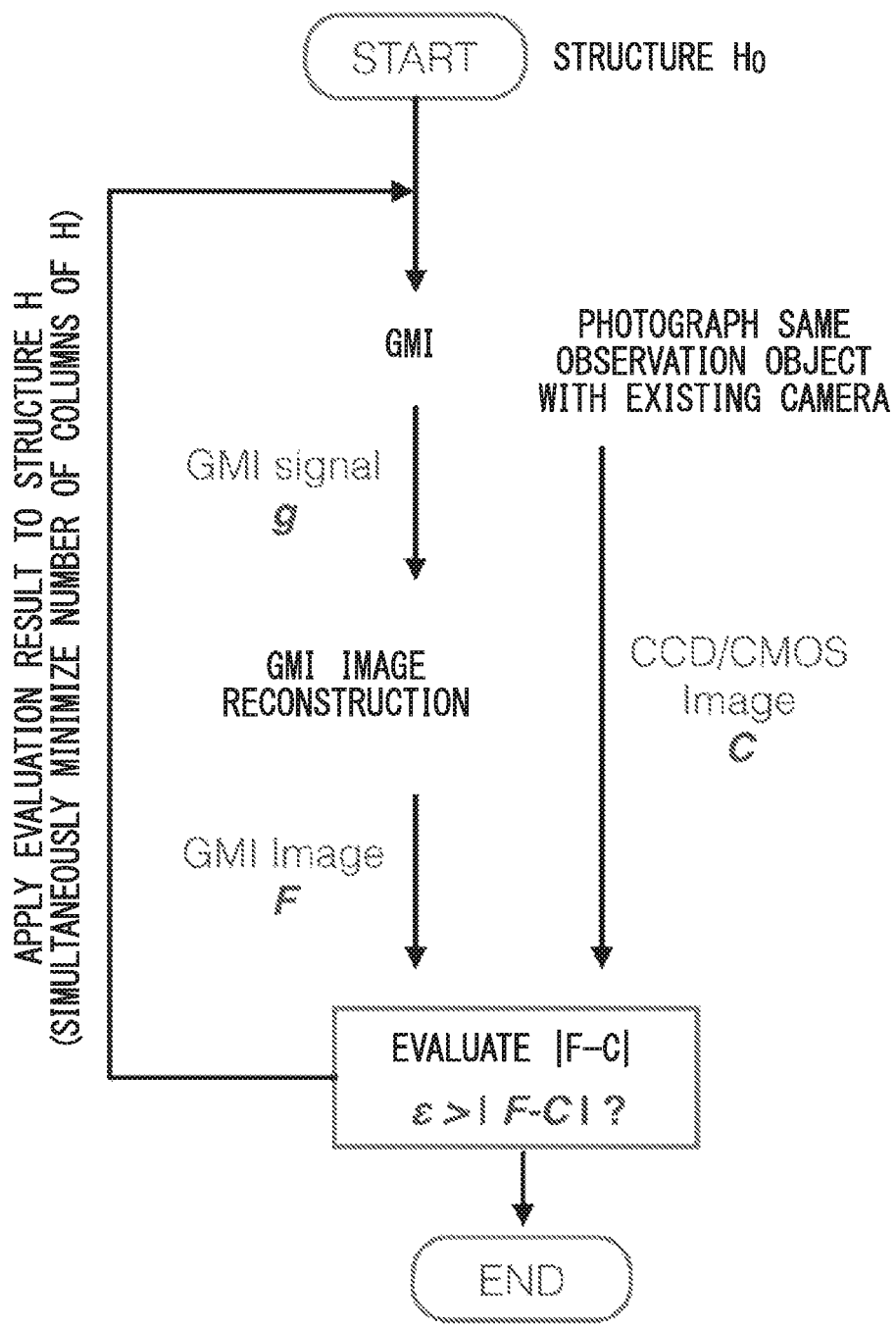
FIG. 11 is a conceptual diagram showing an example of a process of optimizing an illumination pattern.

FIG. 11 is a conceptual diagram showing an example of a process of optimizing the illumination pattern. In this example, an optical signal (a GMI signal, a ghost motion imaging signal, and g) is obtained using the above-described imaging device, and an image (F) obtained by reconstructing the observed object 5 is obtained. On the other hand, the imaging unit images the same observed object 5 and obtains a captured image (C) of the observed object. Then, the optical system control unit compares the reconstructed image (F) with the captured image (C). In this comparison, for example, after the reconstructed image (F) and the captured image (C) are adjusted to have the same size, it is only necessary to obtain a sum of contrast differences of colors or intensities included in pixels (or to obtain a sum of absolute values of the differences or a sum of squares of the differences) and set the obtained value as a comparison value (c). Then, the optical system control unit appropriately changes the illumination pattern and obtains the comparison value again using the same observed object as the previous observed object 5 or using the same type of observed object. In this manner, after a plurality of combinations of illumination patterns and comparison values are obtained, it is only necessary to determine an optimum illumination pattern in consideration of an amount of information of the illumination pattern.

Also, on the basis of the reconstructed image (F), the size of the observed object may be ascertained and the illumination pattern may be controlled so that the illumination pattern becomes an illumination pattern corresponding to the ascertained size. For example, it is only necessary to obtain reconstructed images for one or more observed objects, analyze the size of a necessary irradiation region from these images, and control the illumination pattern so that the illumination pattern has the analyzed size. In this case, the optical system control unit controls the optical system so that the illumination pattern becomes an obtained optimized illumination pattern. The light source system adjusts the illumination pattern in accordance with a control signal from the optical system control unit. In this manner, it is possible to obtain an optimized illumination pattern.

Figure 12:
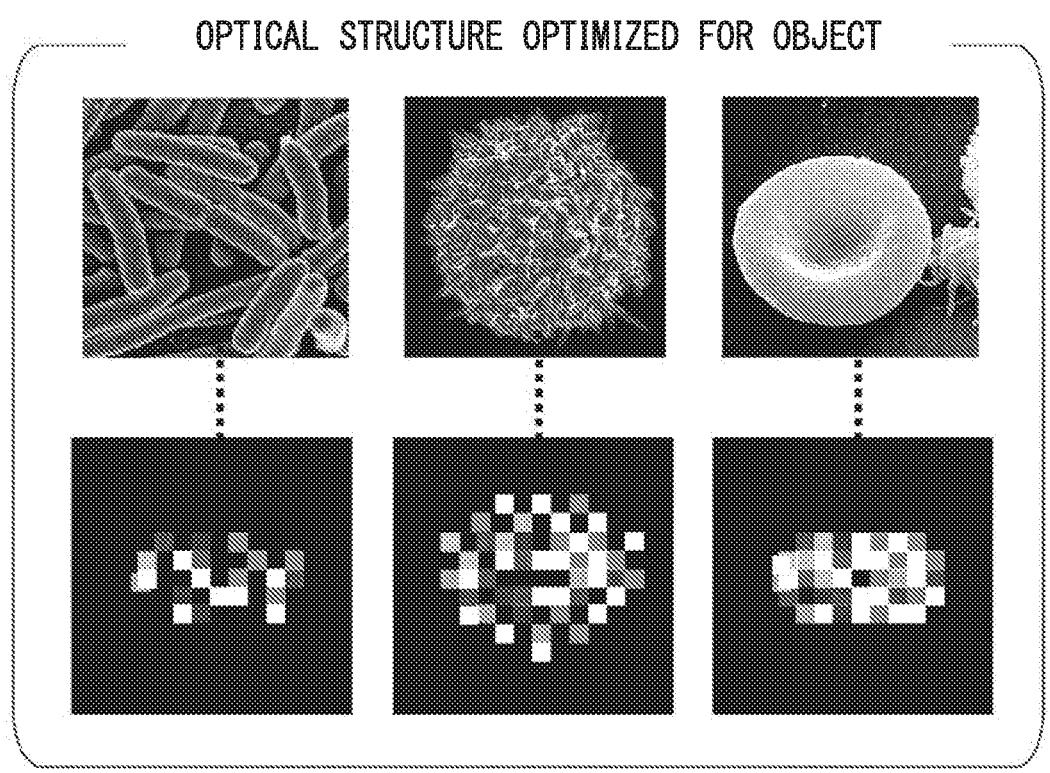
FIG. 12 is a drawing of a captured image showing an example in which an illumination pattern is actually optimized for various observed objects.

FIG. 12 is a drawing of a captured image showing an example in which an illumination pattern is actually optimized for various observed objects. In this example, image reconstruction is first performed a plurality of times to ascertain a range of the size of the observed object. This can be easily implemented by analyzing a region where a reconstructed image exists. Then, a size of the illumination pattern capable of covering a region necessary for imaging the observed object is obtained, the illumination pattern included in the size is varied to obtain the comparison value (s), and an optimum illumination pattern is found from the comparison value (s) of the illumination pattern. Using this optimized illumination pattern, the amount of information can be significantly reduced, the amount of processing required for reconstructing subsequent images can be significantly reduced, and high-speed imaging can be performed.

In a preferred example of this imaging device, the size of the observed object is first ascertained on the basis of the above-described method, and the size of the irradiation pattern is adjusted. Thereafter, the pattern itself in the illumination pattern across the adjusted size (region) is changed to obtain the comparison value (ε) in a plurality of patterns. Moreover, it is only necessary to obtain an optimum illumination pattern by comparing with the comparison value (ε). The comparison value (ε) may be the sum of squares of the difference values of the pixels.

Figure 13:
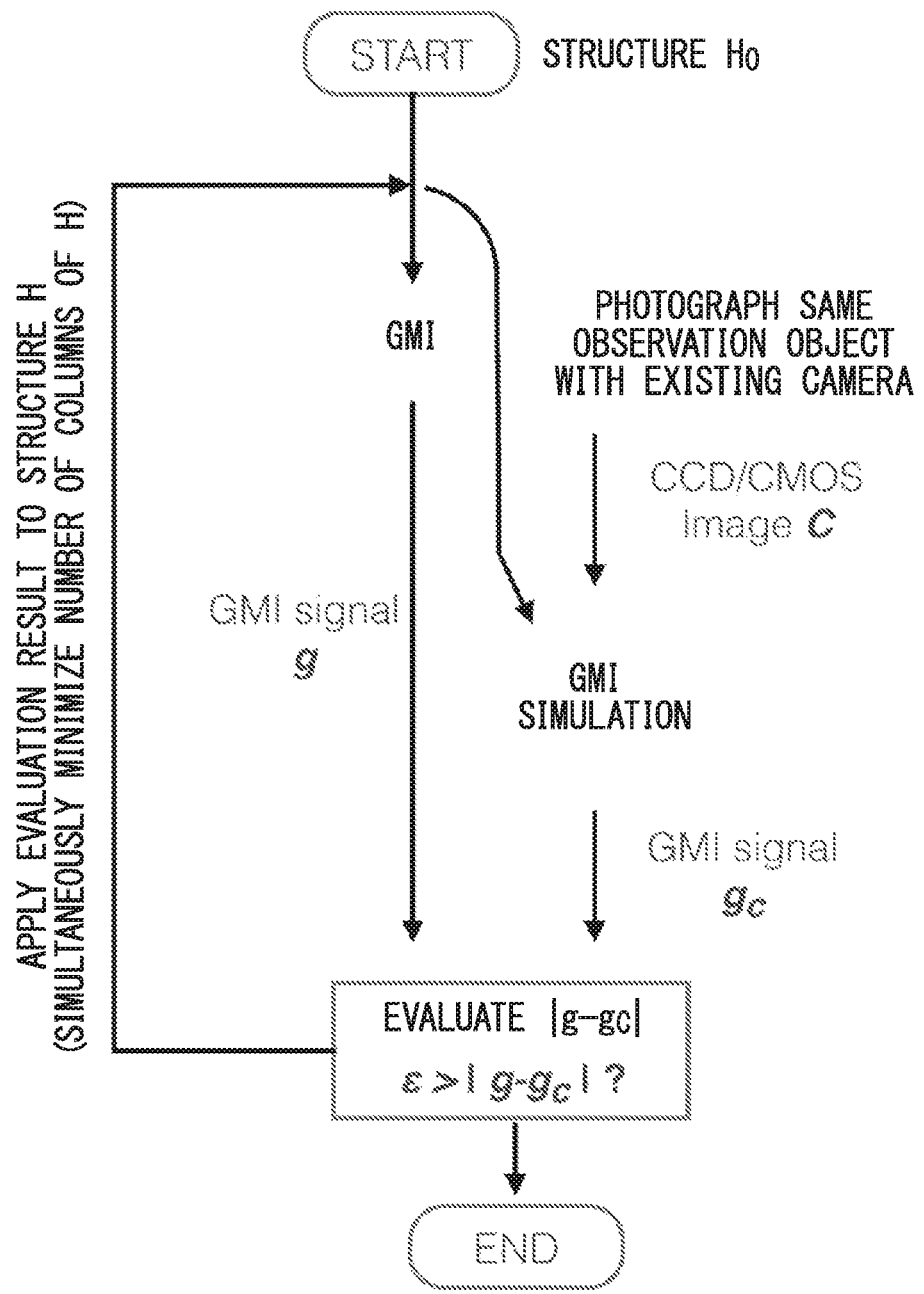
FIG. 13 is a conceptual diagram showing an example of a process of optimizing an illumination pattern.

FIG. 13 is a conceptual diagram showing an example of a process of optimizing an illumination pattern. In this example, the illumination pattern is optimized on the basis of an optical signal (a GMI image) without reconstructing the image. This example further includes a detection system configured to image the observed object 5, an estimated signal calculation unit configured to obtain an estimated signal $g_C$ obtained by estimating the optical signal detected by one or a few pixel detection elements on the basis of a captured image of the observed object imaged by the detection system, and an arithmetic unit configured to change the illumination pattern while comparing optical signals g detected by one or a few pixel detection elements and the estimated signal $g_C$ estimated by the estimated signal calculation unit.

In this example, for example, the detection system images an observed object and obtains a captured image. Then, image analysis is performed on the captured image, and a composition or tissue of each part is ascertained. Then, light information corresponding to each composition or tissue is obtained from a table storing information about light (e.g., fluorescence) emitted from each composition and tissue when light irradiation is performed or the like. In this manner, it is possible to ascertain a type of light response when light is radiated to the observed object. Then, it is possible to estimate the optical signal g on the basis of the captured image. This is the estimated signal $g_C$ estimated by the estimated signal calculation unit. The optical signal g is, for example, a spectrum as shown in FIG. 7. Then, it is only necessary for the second illumination pattern control unit 107 to obtain the evaluation value (ε) for the estimated signal $g_C$ and the optical signal g after adjustment is performed so that a corresponding positional relationship between the estimated signal $g_C$ and the optical signal g is correct by adjusting relative intensities of the estimated signal $g_C$ and the optical signal g to the same degree and further performing automatic matching of the shape of the spectrum (performing adjustment so that an amount of overlapping is maximized). For example, ε may be a sum of differences between the relative intensities of the estimated signal $g_C$ and the optical signal g per unit time (or an absolute value of a difference or a square of the difference). Alternatively, for example, the estimated signal $g_C$ and the optical signal g may be converted into a new coordinate domain to achieve a difference in a relative intensity or the like in the domain. It is only necessary to obtain the evaluation value (ε) on the basis of various illumination patterns and optimize the illumination pattern using the evaluation value (ε).

Figure 14:
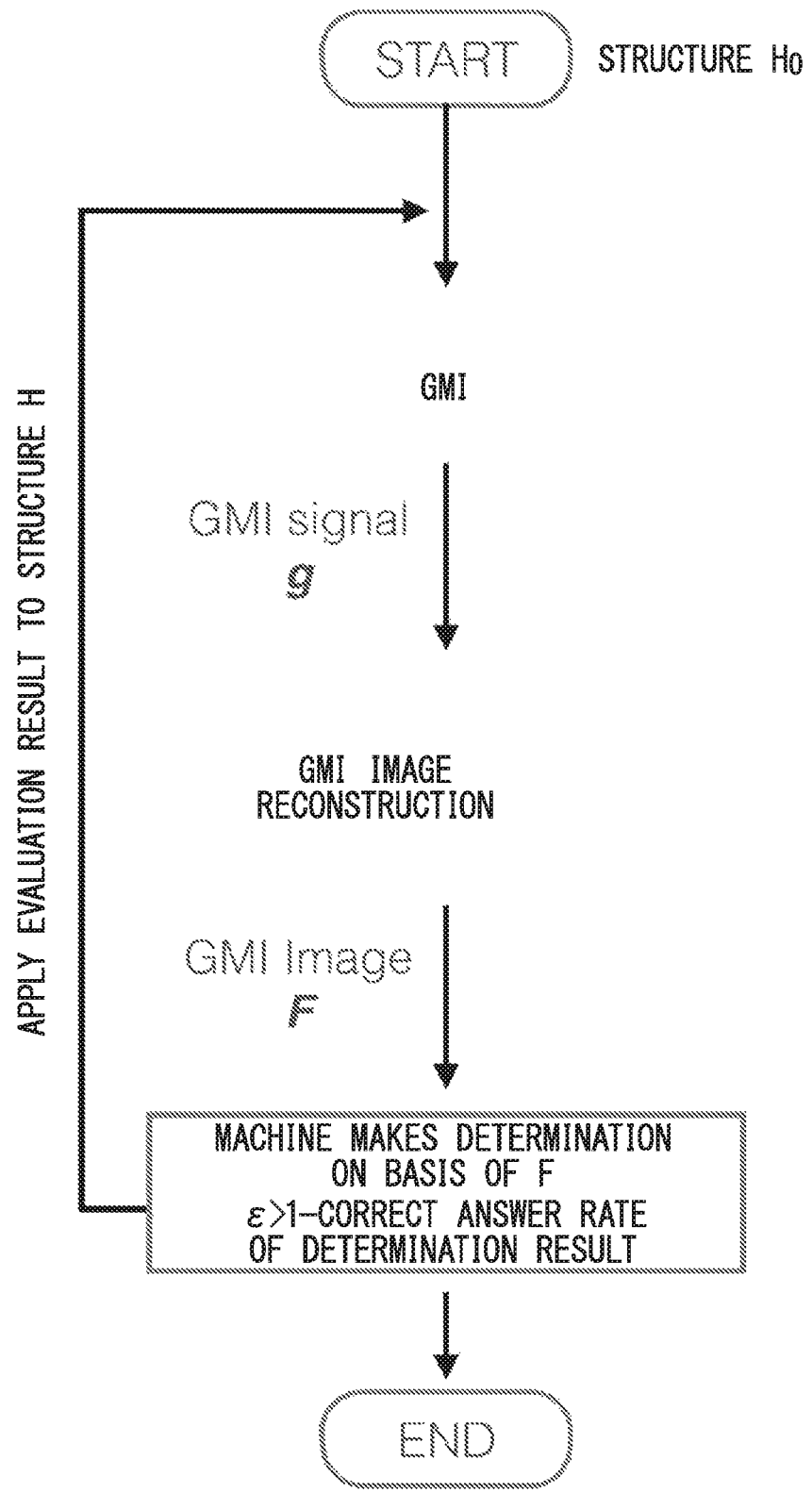
FIG. 14 is a conceptual diagram showing an example of a process of optimizing an illumination pattern.

FIG. 14 is a conceptual diagram showing an example of a process of optimizing the illumination pattern. This example is used, for example, when information about an observed object (for example, a pattern of an image obtained by reconstructing the observed object in an image reconstruction unit) has already been stored. That is, this example further includes a control unit configured to change the illumination pattern using an image (F) of the observed object reconstructed by the image reconstruction unit. In this example, for example, the control unit performs pattern authentication with the image (F) of the reconstructed observed object and a pattern of the image stored in advance. Because the pattern authentication technology is well-known, pattern authentication can be implemented by installing a well-known pattern authentication program in a computer. This example can be effectively used, for example, when an object (an accepted item or a rejected item) is selected or when inspecting for the presence or absence of an object. Also, this example can be used for the purpose of automatically measuring the number of cells contained in a specific region. That is, a preferred example of the imaging device further includes an observed object determination unit configured to classify an observed object using the image of the observed object reconstructed by the image reconstruction unit.

Figure 15:
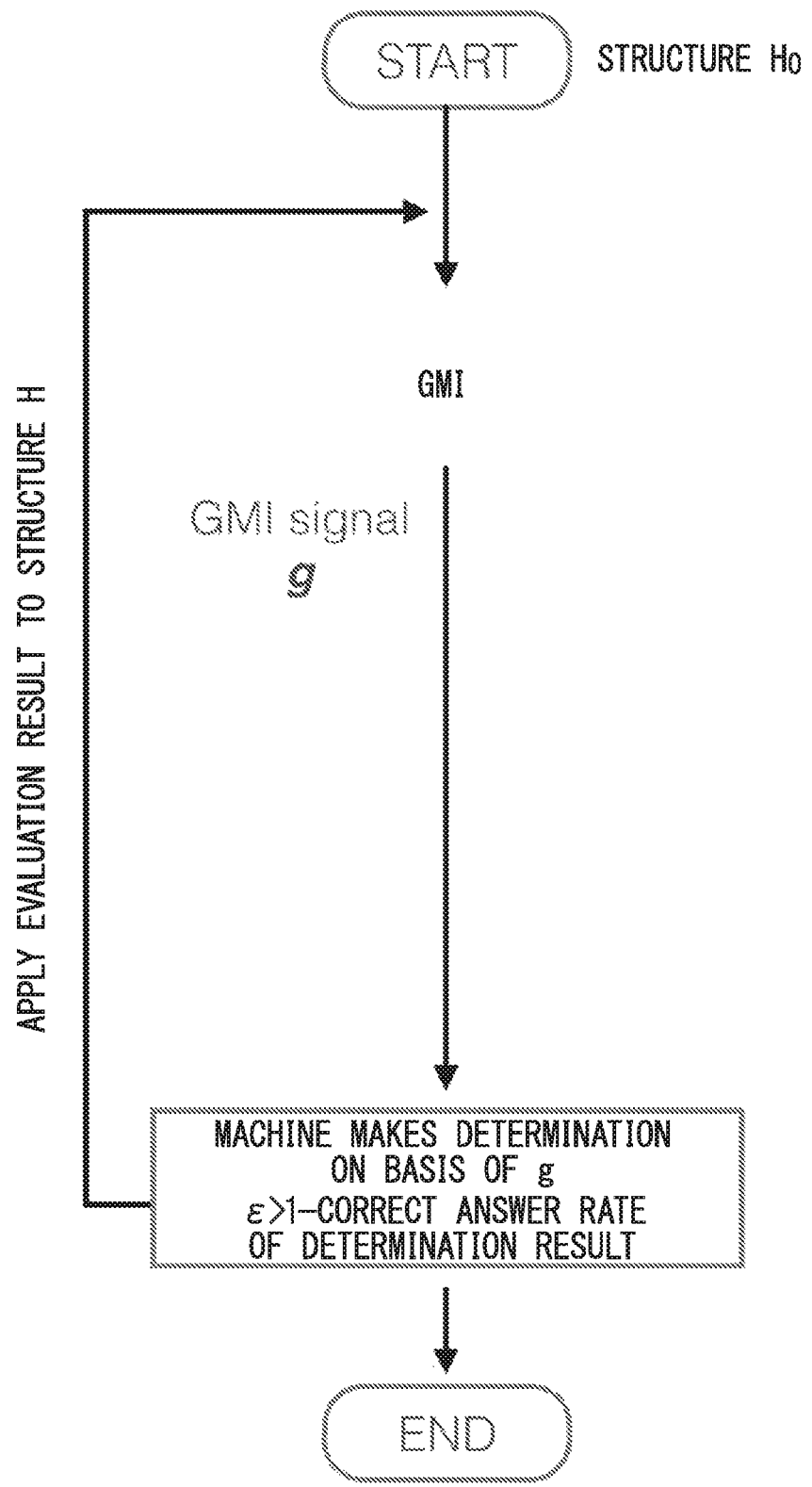
FIG. 15 is a conceptual diagram showing an example of a process of optimizing an illumination pattern.

FIG. 15 is a conceptual diagram showing an example of a process of optimizing the illumination pattern. This example is used, for example, when information about the observed object (for example, the pattern of the optical signal g) has already been stored. This example further includes a control unit configured to change the illumination pattern using the optical signal g detected by one or a few pixel detection elements. In this example, for example, the control unit performs pattern authentication with a pattern of the optical signal g detected by one or a small number of pixel detection elements and the optical signal g stored in advance. Because the pattern authentication technology is well-known, pattern authentication can be implemented by installing a well-known pattern authentication program in a computer. Alternatively, for example, the two signals g may be converted into a new coordinate domain to achieve a difference in a relative intensity or the like within the domain.

Also, a preferred example of the imaging device further includes a reconstructed image classification unit configured to classify the reconstructed image of the observed object using a plurality of images of the observed object reconstructed by the image reconstruction unit. The image (F) classified by the reconstructed image classification unit is used by the control unit or/and the determination unit.

A preferred usage form of this analysis device is a flow cytometer having any one of the above-described analysis devices. This flow cytometer has a flow cell including the light irradiation region 3.

The flow cytometer preferably includes a sorting unit configured to recognize an observed object on the basis of an analysis result of the analysis unit 11 and sort the observed object 5. More specifically, when the observed object 5 is a target object and when the observed object 5 is not a target object, the target object can be sorted by making a path after passing through the sorting unit different.

In the flow cytometer, the target object may be analyzed in advance and information indicating the target object (a threshold value or the like) may be stored in the storage unit. Also, an object including a large number of target objects may be observed, the classification unit may recognize the object as the observed object, and classification information about the target object may be subjected to a machine learning algorithm. This classification information is, for example, a characteristic peak included in various spectra.

When the observed object moves through the flow cell and reaches the light irradiation region, light from the light source is radiated to the observed object. Then, the light-receiving unit receives an optical signal from the observed object. The analysis unit analyzes the optical signal. At that time, the analysis unit reads the classification information of the target object stored in the storage unit and determines whether the observed object is a target object by comparing the classification information with the optical signal. If the analysis unit determines that the observed observed object is the target object, the analysis unit sends a control signal corresponding to the observed object serving as the target object to the classification unit. The classification unit receiving the control signal adjusts the path and guides the observed object to the path of the target object. In this manner, it is possible to recognize the target object and an object other than the target object and classify the objects.

At this time, it is only necessary to measure a plurality of observed objects and appropriately optimize the optical system or the detection system in the analysis unit. Then, the classification can be rapidly performed with appropriate accuracy.

Example 1

Hereinafter, the present invention will be specifically described with reference to examples.

<Example 1-1> Supervised Machine Learning, Decompression/Conversion of Image into Temporal Signal Using Optical Structure, Classifier Formation, and Classification A computer used in present example included a 2.8 GHz Intel Core i7 processor and 16 GB of memory.

Figure 16:
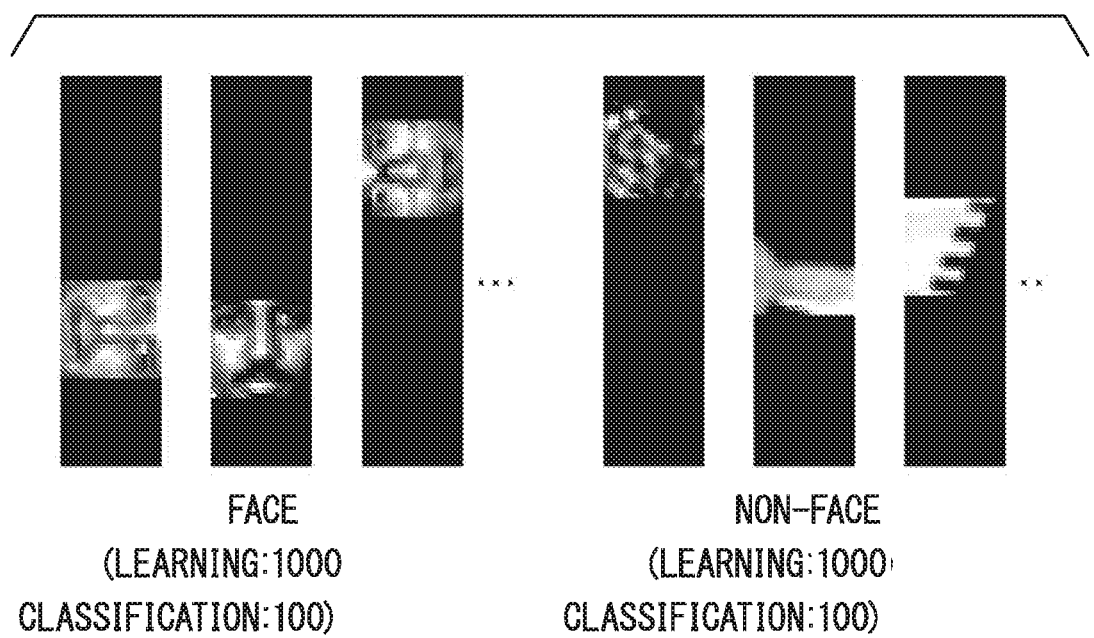
FIG. 16 is a diagram showing an example of an object sample for learning.

First, as an object sample for learning, a total of 1100 images including 1000 images for learning and 100 images for classification accuracy measurement were provided for a face image group and a non-face image group in which an image had 19 pixels in length and 19 pixels in width (an image source of FIG. 16 is the Center for Biological and Computational Learning at MIT).

Figure 17:
FIG. 17 is a diagram showing an example of an optical structure.

Within the computer, noise (S/N=30 dB) was applied to the above-described image group, the above-described GMI process passing through an optical structure was virtually executed, and a temporal signal was generated. The optical structure was a patterned illumination optical structure or detected optical structure in an experimental system, the optical structure used here was 19 pixels in width and 343 pixels in length (FIG. 17), and the temporal signal was generated for (1×192) pixels (which are the same as those of the original image). A face or non-face label was attached to all waveform signals, and a classifier was formed by learning 1000 waveforms for learning using a linear classification type support vector machine technique. As a sample for classification accuracy measurement, a temporal signal was provided using the same optical structure on the basis of 100 new face and non-face images. The label was removed from this sample, the formed classifier performed automatic classification, and a correct answer rate of the label (face or non-face) was measured.

On the other hand, a classifier was formed by giving noise (S/N=30 dB) to the same image sample, attaching a face or non-face label thereto, and learning 1000 images for learning using a support vector machine technique. As a sample for classification accuracy measurement, 100 new face and non-face images were similarly provided. The label was removed from this sample, the formed classifier performed automatic classification, and a correct answer rate of the label (face or non-face) was measured.

The result was that the classification accuracy for a face or non-face temporal signal (the number of correct answers for face and non-face/total number×100) in the classifier learning the temporal signal sample was 87% and the classification accuracy for the face or non-face of the image in the classifier performing learning was 82%. According to this result, it was found that, even if a temporal signal generated by passing an image through the optical structure was learned and classified, it was possible to obtain a classification result at least equivalent to that of learning and classifying the original image.

Also, a time required for learning 1000 samples and classifying 100 samples was not different between in the case of the image or in the temporal signal.

<Example 1-2> Supervised Machine Learning, Compression/Conversion of Image into Temporal Signal Using Optical Structure, Classifier Formation, and Classification A computer used in the present example included a 2.8 GHz Intel Core i7 processor and 16 GB of memory. First, as an object sample for learning, a total of 1100 images including 1000 images for learning and 100 images for classification accuracy measurement were provided for a face image group and a non-face image group in which an image has 19 pixels in length and 19 pixels in width (FIG. 16).

Figure 18:
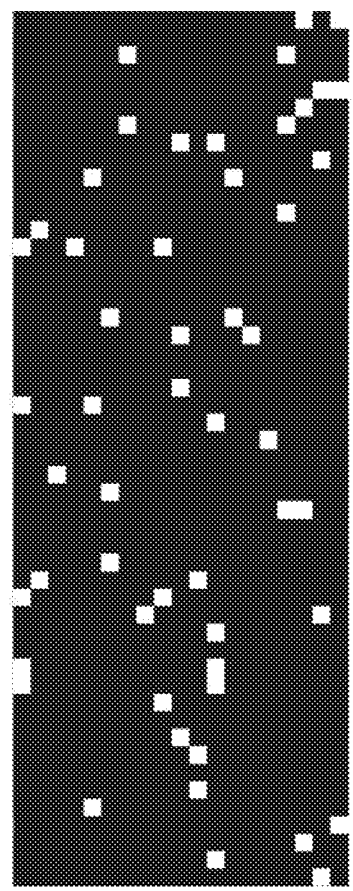
FIG. 18 is a diagram showing an example of an optical structure.

Within the computer, noise (S/N=30 dB) was applied to the above-described image group, the above-described GMI process passing through an optical structure was virtually executed, and a temporal signal (e.g., a GMI waveform) was generated. The optical structure was a patterned illumination optical structure or a detection optical structure in the experimental system, and the optical structure used here had 19 pixels in width and 50 pixels in length (FIG. 18), and the temporal signal was generated in 68 pixels and 81% of a total number of original image pixels were compressed. A face or non-face label was attached to all compressed temporal signals and a classifier was formed by learning 1000 waveforms for learning using the support vector machine technique. As a sample for classification accuracy measurement, a compressed temporal signal was provided using a similar optical structure on the basis of 100 new face and non-face images. The label was removed from this sample, the formed classifier performed automatic classification, and a correct answer rate of the label (face or non-face) was measured.

On the other hand, a classifier was formed by giving noise (S/N=30 dB) to the same image sample, attaching a face or non-face label thereto, and learning 1000 images for learning using a linear classification type support vector machine technique. As a sample for classification accuracy measurement, 100 new face and non-face images were similarly provided. The label was removed from this sample, the formed classifier performed automatic classification, and a correct answer rate of the label (face or non-face) was measured.

The result was that the classification accuracy for a compressed temporal waveform signal of the face or non-face (the number of correct answers for face and non-face/total number×100) in the classifier learning the compressed temporal waveform signal sample was 75% and the classification accuracy for the face or non-face of the image in the classifier learning the image sample was 82%. According to this result, it was found that the classification accuracy using machine learning can also maintain equivalent accuracy according to optical image compression through the optical structure.

Also, a time taken to learn 1000 temporal waveform samples was 399 seconds and a time taken to learn 1000 image samples was 475 seconds. According to this result, it was found that it is possible to shorten the time by 16% as compared with the original image in the case of the compressed time signal in the learning of the same sample.

Furthermore, a time taken to classify 100 compressed temporal samples was 0.0065 seconds, and a time taken to classify 100 image samples was 0.0147 seconds. According to this result, it was found that it is possible to shorten the time by 56% compared with the original image classification in the case of compressed time signal classification in the classification of the same sample.

Example 2

Example 2 Cell Classification by Unsupervised Machine Learning

A computer used in this embodiment included a 2.8 GHz Intel Core i7 processor and 16 GB of memory.

Figure 19:
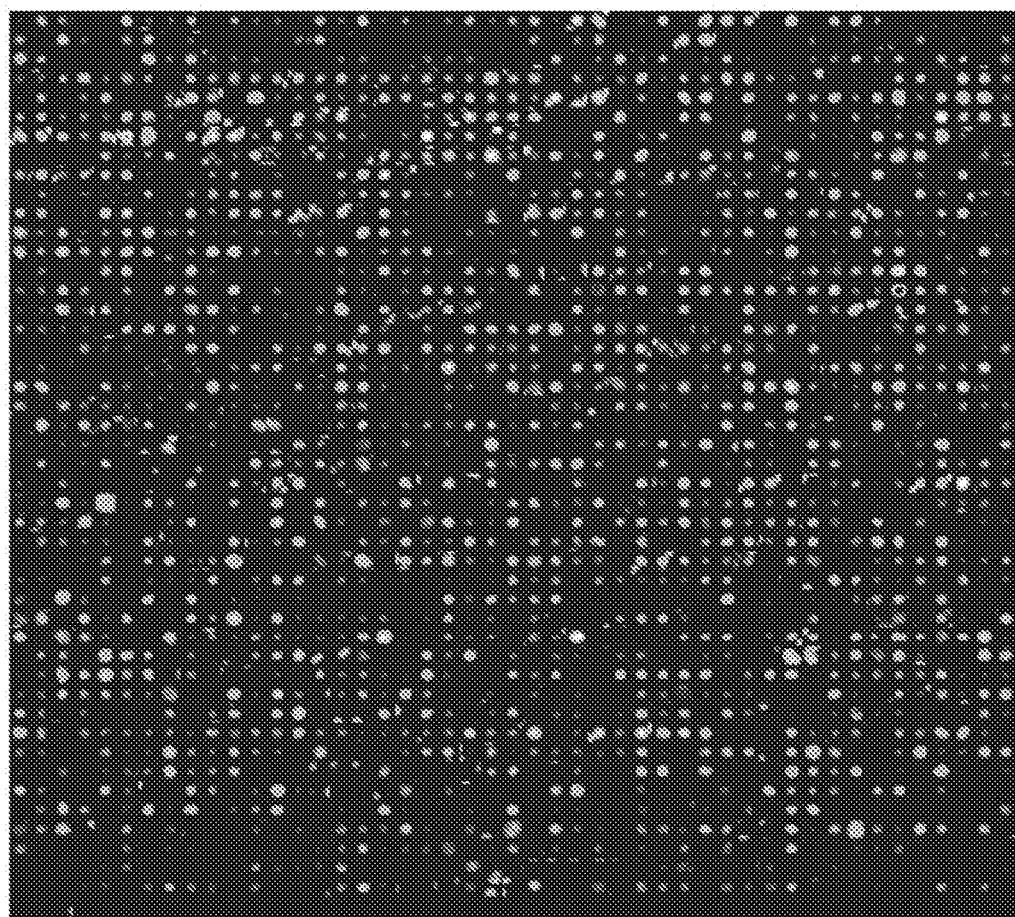
FIG. 19 is a diagram showing an example of a large number of single-cell image group samples.

For a sample, viable cell staining was performed using calcein AM for a single-cell group generated by dispersing mouse spleen. A fluorescence-labeled single cell solution as described above was spread on a glass slide and a large number of fluorescence images of a single-cell group were captured by an sCMOS camera (Flash 4.0 manufactured by Hamamatsu Photonics K.K.) using a fluorescence microscope. This image data was read within the computer, the position of a single cell was specified by software (imagej), and a single-cell periphery was partitioned using 70 pixels in length and width to cut out 2165 samples of a large number of single-cell image group samples (FIG. 19). This single-cell image group included images containing single cells having different sizes and images including a plurality of cells or objects other than cells.

Figure 20:
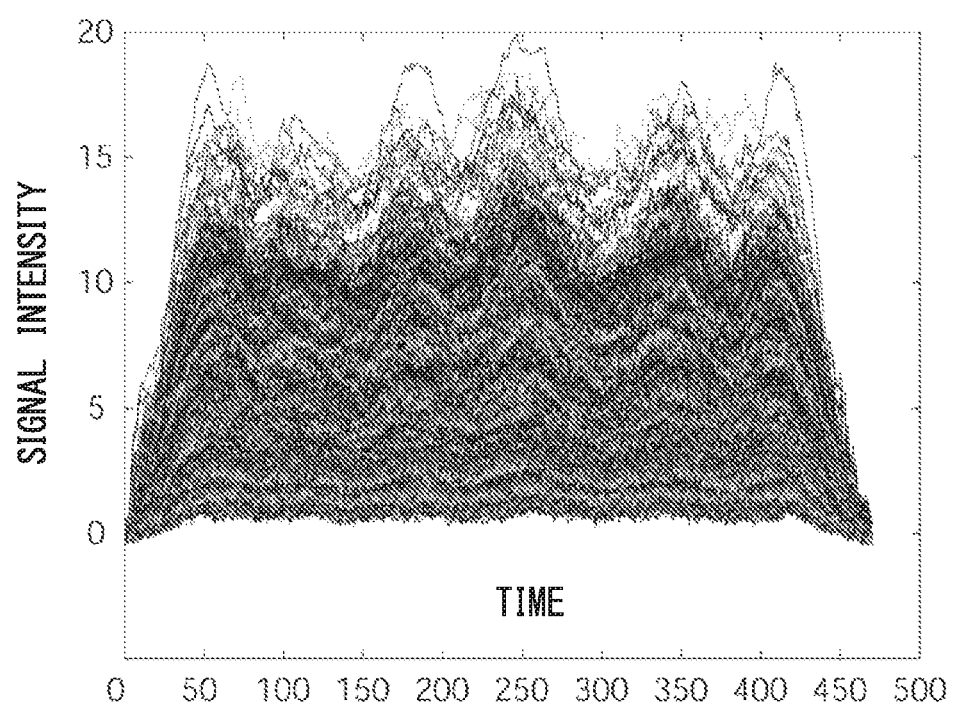
FIG. 20 is a diagram showing an example of an optical structure.
Figure 21:
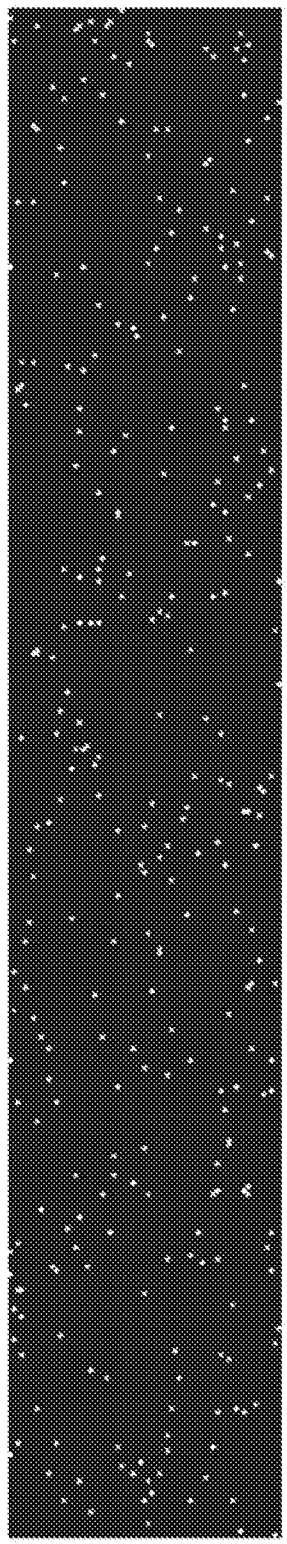
FIG. 21 is a diagram showing an example of a group of virtual flow cytometry cell temporal waveforms.

Within the computer, noise (S/N=30 dB) was applied to the above-described image group, the above-described GMI process passing through an optical structure was virtually executed, a temporal signal (e.g., a GMI waveform) was generated, and a temporal waveform group of virtual flow cytometry cells was provided (FIG. 20). The optical structure used here had 70 pixels in length and 400 pixels in width, and the temporal signal had 470 pixels (FIG. 21). (On the other hand, noise (S/N=30 dB) was applied to the same image sample, and a virtual flow cytometry cell image was provided.)

Figure 22:
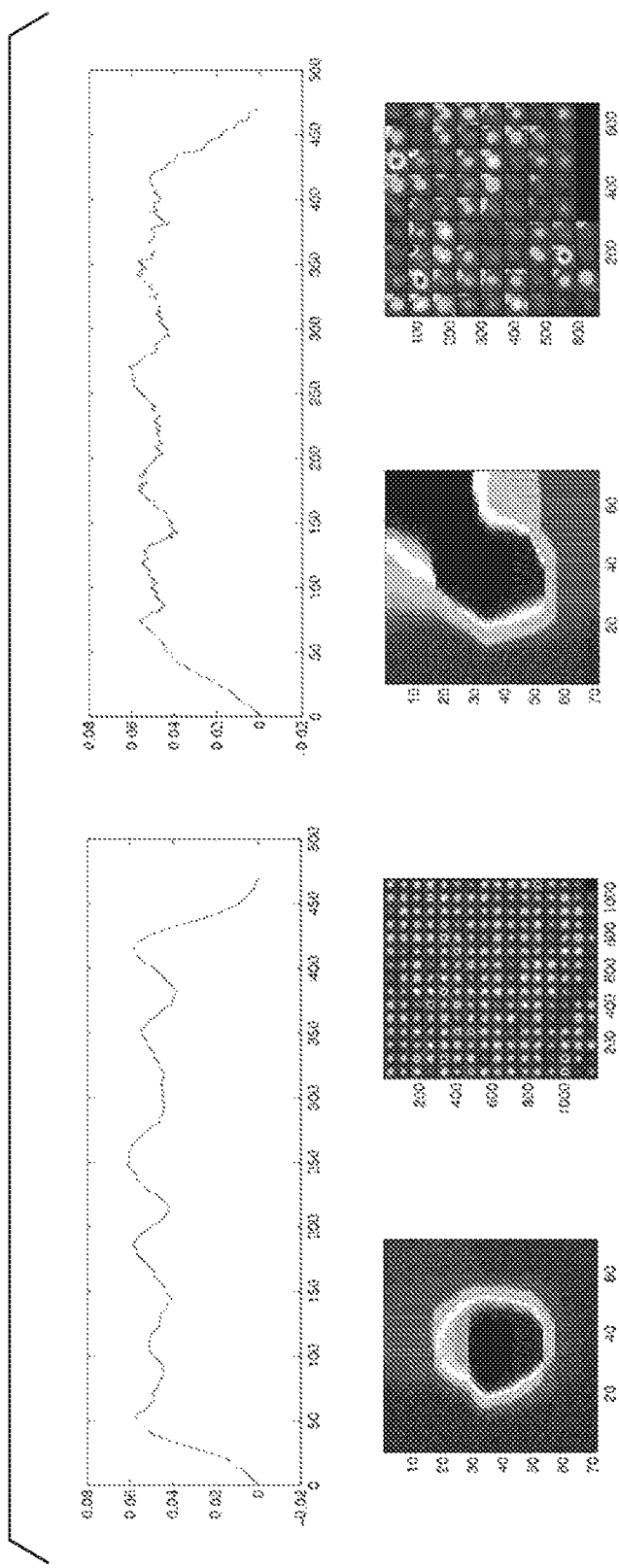
FIG. 22 is a diagram showing an example of a cell group (lower right) classified, an average signal (top) of time-series signals generated by the cell group, and a cell image reconstructed on the basis of the average signal.
Figure 23:
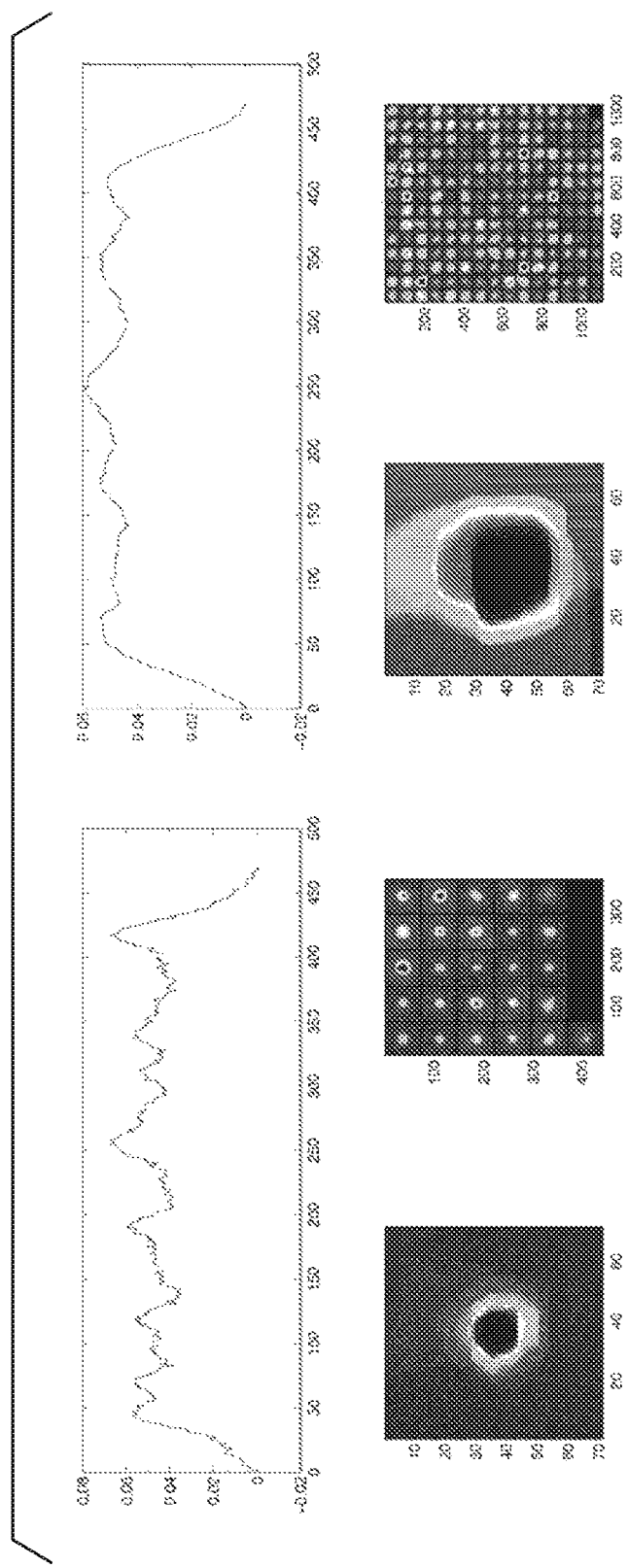
FIG. 23 is a diagram showing an example of a cell group (lower right) classified, an average signal (top) of temporal signals generated by the cell group, and a cell image reconstructed on the basis of the average signal.

Single-cell temporal waveform samples provided as described above were classified using unsupervised machine learning classification using software (matlab). Specifically, the single-cell temporal waveform samples were classified into 20 types of cell groups using a k-means technique. A representative (average) temporal signal was generated from the cell temporal waveform group included in each same classification group and a cell image was generated on the basis of this temporal signal (FIGS. 22 and 23). As a result, it is can be seen that single cells, a plurality of cells, waste, a cell size, or the like are correctly classified. These are one of the greatest error sources in conventional cytometry and it was showed that correct classification is also made in unsupervised machine learning using a compressed temporal waveform signal through an optical structure.

Example 3

Example 3 Optimization of Optical Structure by Supervised Machine Learning

In the present example, samples similar to those used in Example 1 were used.

Figure 24:
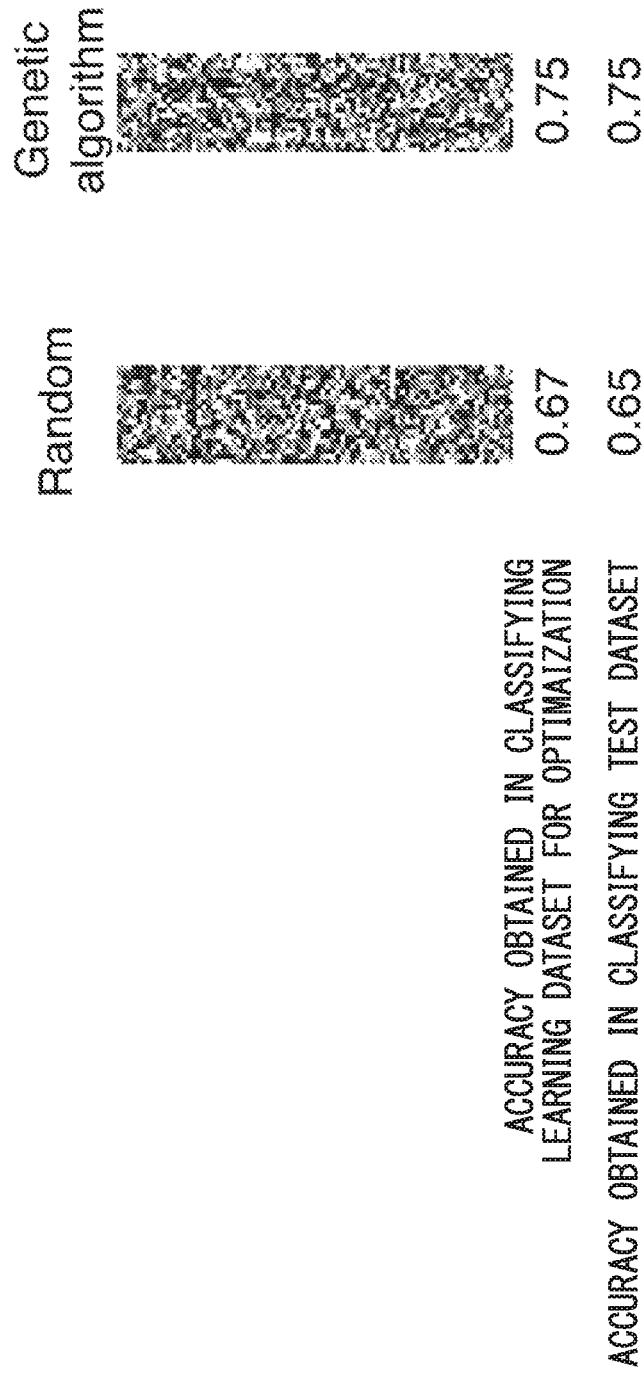
FIG. 24 is a diagram showing an example of optical structures before and after optimization and an effect of optimization on classification accuracy.

As an initial optical structure, a random structure was provided with 80 pixels in length and 20 pixels in width and samples of the temporal waveform signal group were provided through the image samples of Example 1. As in Example 1, learning was performed using a linear classification type support vector machine technique, and the classification accuracy (the number of correct answers for face and non-face/total number×100) was obtained. This accuracy of classification was set as an objective function, and the optical structure was optimized using machine learning in order to maximize the objective function (FIG. 24). Specifically, a genetic algorithm was used. The number of individuals was 200, the number of generations was 16,000, roulette selection was used for selection, and uniform crossover was used for crossover. As a result, as in Example 1, evaluation was performed using image samples unused for optimization. The classification accuracy was 65% in the initial random optical structure, the classification accuracy was 75% in the optical structure after optimization, and an improvement in classification accuracy of 10% was exhibited.

Next, an example of the analysis unit 11 will be described with reference to FIG. 25.

Figure 25:
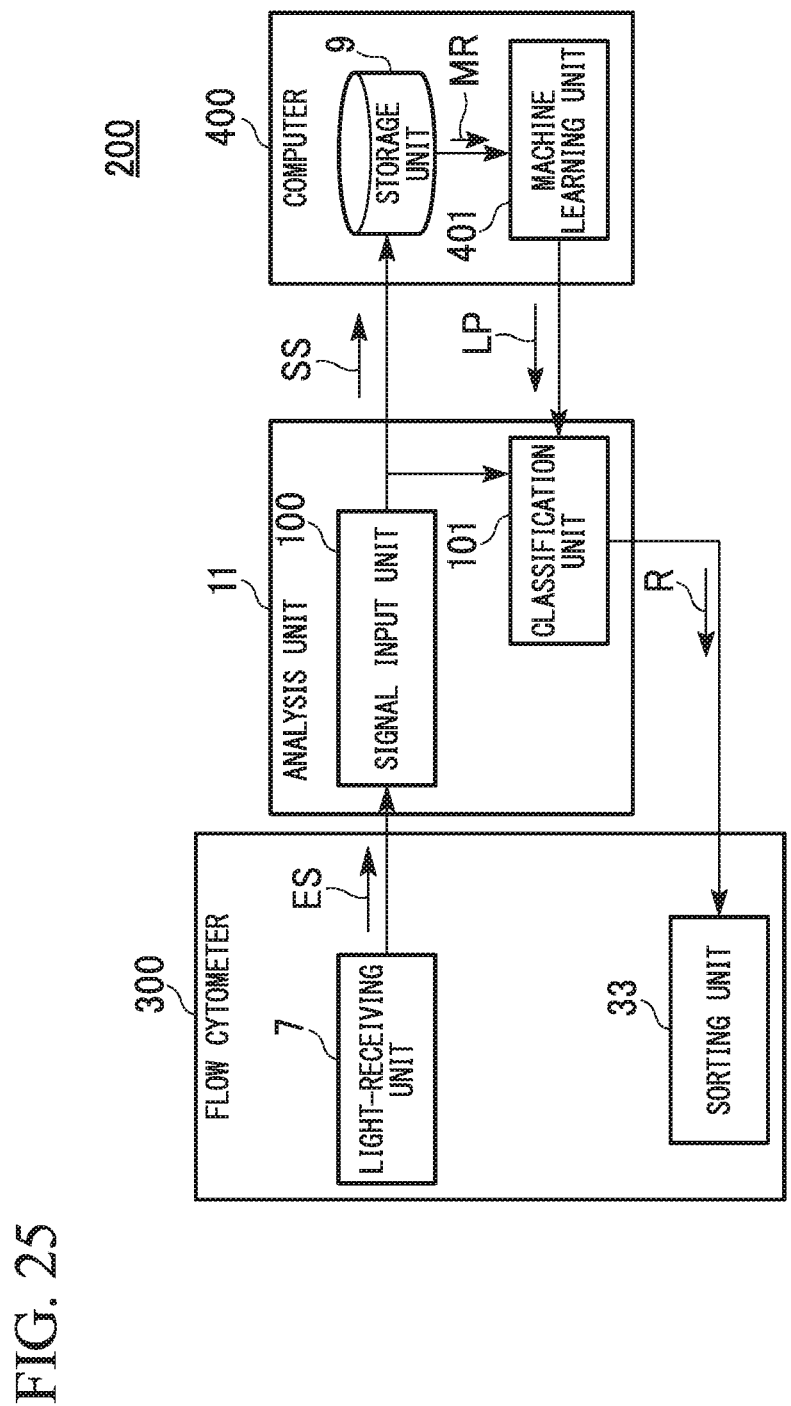
FIG. 25 is an example showing an example of an analysis system.

FIG. 25 shows an example of an analysis system 200.

The analysis system 200 includes a flow cytometer 300, the analysis unit 11, and a computer 400. The flow cytometer 300 observes and sorts the observed object 5. The flow cytometer 300 outputs an optical signal related to the observed object 5 to the analysis unit 11. The analysis unit 11 classifies the observed object 5 from the flow cytometer 300 on the basis of an optical signal related to the observed object 5. The computer 400 mechanically learns the optical signal related to the observed object 5 observed by the flow cytometer 300. The computer 400 changes a classification algorithm of the classification unit 101 on the basis of a machine learning result.

The flow cytometer 300 includes a light-receiving unit 7 and a sorting unit 33.

The light-receiving unit 7 receives the optical signal from the observed object 5 and converts the received optical signal into an electrical signal ES. The light-receiving unit 7 outputs the electrical signal ES obtained through the conversion to a signal input unit 100.

The sorting unit 33 sorts the observed object 5 on the basis of a signal classification result R indicating the result of analyzing the electrical signal ES in the analysis unit 11.

The computer 400 includes a storage unit 9 and a machine learning unit 401.

The storage unit 9 stores an input signal SS. The machine learning unit 401 performs machine learning on the optical signal stored in the storage unit 9.

In this example, the analysis unit 11 includes the signal input unit 100 and a classification unit 101. The classification unit 101 includes a logic circuit capable of changing a logic circuit configuration. The logic circuit may be a programmable logic device such as a field-programmable gate array (FPGA), or an application specific integrated circuit (ASIC).

The machine learning unit 401 changes the classification algorithm of the classification unit 101 included in the analysis unit 11 on the basis of the machine learning result. In this example, the machine learning unit 401 changes the logic circuit configuration of the classification unit 101 on the basis of the machine learning result. Specifically, the machine learning unit 401 configures a classification logic LP, which is a logic circuit configuration of a classification algorithm suitable for the observed object 5, on the basis of the machine learning result, and changes the logic circuit.

The signal input unit 100 acquires the electrical signal ES from the light-receiving unit 7. The signal input unit 100 outputs the electrical signal ES acquired from the light-receiving unit 7 as an input signal SS to the storage unit 9 and the classification unit 101.

The signal input unit 100 may remove noise of the electrical signal ES by applying a filter to the electrical signal ES. The noise is, for example, high-frequency noise, shot noise, and the like. By removing the noise of the electrical signal ES, the signal input unit 100 can stabilize a trigger position at which the electrical signal ES starts to be acquired as the input signal SS. The signal input unit 100 can output a signal suitable for machine learning as the input signal SS by stabilizing the trigger position.

Also, the signal input unit 100 may distinguish whether the observed object 5 is a single cell or a plurality of cells and whether the observed object 5 is waste and distinguish a cell size of the observed object 5 and the like, and determine whether or not to output the signal as the input signal SS.

The above-described filter is changed in accordance with the observed object 5. The filter removes noise by making the electrical signal ES have a gentle waveform. Specifically, the filter is a filter for performing comparison with the threshold value of the electrical signal ES, a filter for performing a moving average operation on the electrical signal ES and comparing a value obtained through the moving average operation with a threshold value, a filter for differentiating the value obtained through the moving average operation on the electrical signal ES and comparing the differentiated value with a threshold value, or the like.

The classification unit 101 acquires the input signal SS from the signal input unit 100. The classification unit 101 classifies the observed object 5 observed by the flow cytometer 300 on the basis of the input signal SS acquired from the signal input unit 100.

The classification unit 101 classifies the input signal SS through the logic circuit, thereby determining the observed object 5. By classifying the observed object 5 through the logic circuit, the classification unit 101 can classify the observed object 5 at a higher speed than in a general-purpose computer.

As described above, the light-receiving unit 7 receives scattered light, transmitted light, fluorescence, or electromagnetic waves from the observed object located in the light irradiation region irradiated with the light from the light source, and converts the received light or electromagnetic waves into an electrical signal. The analysis unit 11 analyzes the observed object 5 on the basis of a signal extracted on the basis of a time axis of the electrical signal ES output from the light-receiving unit 7.

Also, the analysis unit 11 includes the signal input unit 100. The signal input unit 100 filters the electrical signal ES output by the flow cytometer 300. The signal input unit 100 filters the electrical signal ES to output a signal with reduced noise as the input signal SS to the classification unit 101 and the storage unit 9. The machine learning unit 401 can perform machine learning on the basis of the input signal SS with reduced noise and can improve the accuracy of classification of the observed object 5. Also, the signal input unit 100 may include a logic circuit. When the signal input unit 100 includes a logic circuit, the filter configuration may be changed on the basis of the machine learning result.

Also, the analysis unit 11 includes the classification unit 101. Because the classification unit 101 includes the logic circuit, the classification unit 101 can classify the observed object 5 in a shorter time than in computation with a general-purpose computer.

Next, the support vector machine technique, which is an example of the classification algorithm of the analysis unit 11 described above, will be described with reference to FIG. 26.

Figure 26:
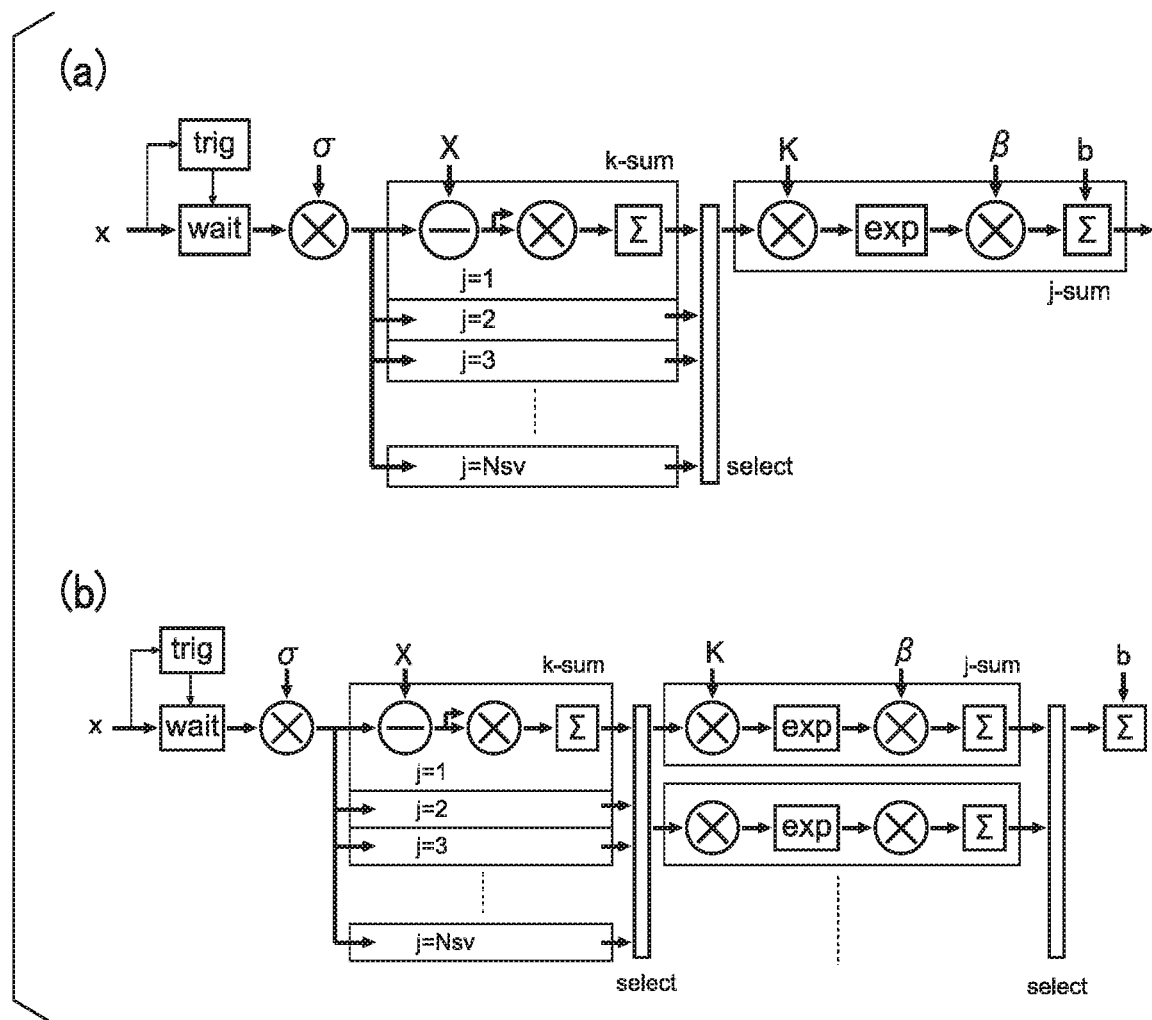
FIG. 26 is a diagram showing an example of a discriminant calculation circuit of an analysis unit.

FIG. 26 is a diagram showing an example of a discriminant calculation circuit of the analysis unit 11.

A discriminant of the support vector machine technique can be represented by Equation (1). Classification is made on the basis of a sign of a result of Equation (1).

[Math. 1]

$$f(x) = b + \sum_{j}^{N_{SV}} \alpha_j Y_j \exp\left[-\sum_{k}^{N_{SL}} \left(\frac{\hat{X}_{jk} - \hat{x}_k}{K}\right)^2\right] \quad (1)$$

b included in Equation (1) is a constant. Here, it is possible to adjust a classification condition of the support vector machine technique by changing b included in Equation (1). For example, if b included in Equation (1) is changed so that the classification condition becomes strict, a false positive rate can be minimized. α and Y included in Equation (1) are values obtained using machine learning.

Here, an element included in Equation (1) in which X is marked with a ^ (hat symbol) thereabove will be described as X(hat). X(hat) included in Equation (1) can be represented by Equation (2).

[Math. 2]

$$\hat{X}_{jk} = \frac{X_{jk} - \mu_k}{\sigma_k} \quad (2)$$

X included in Equation (2) is a matrix obtained using machine learning. X(hat)$_{jk}$ included in Equation (2) is a value obtained by normalizing the matrix X obtained using machine learning.

[Math. 3]

$$\hat{x}_k = \frac{x_k - \mu_k}{\sigma_k} \quad (3)$$

x included in Equation (3) is data input to the analysis unit 11. In this example, the data input to the analysis unit 11 is a signal extracted on the basis of the time axis of the electrical signal output from the light-receiving unit 7. An element included in Equation (3) in which x is marked with ^ (hat symbol) thereabove will be described as x(hat). In Equation (3), x(hat)$_k$ is a value obtained by normalizing x.

Here, if the above-described Equation (1) is implemented as a logic circuit, the logic circuit scale becomes enormous and may not fit an FPGA or PLD logic circuit size. Therefore, a logic circuit based on Equation (4) is mounted on the logic circuit mounted on the classification unit 101.

[Math. 4]

$$f(x) = b + \sum_{j}^{N_{SV}} \beta_j \exp\left[\tilde{K}\sum_{k}^{N_{SL}} \left(\tilde{X}_{jk} - x_k \tilde{\sigma}_k\right)^2\right] \quad (4)$$

An element included in Equation (4) in which K is marked with ~ (tilde symbol) thereabove will be described as K(tilde). An element included in Equation (4) in which X is marked with ~ (tilde symbol) thereabove will be described as X(tilde). An element included in Equation (4) in which σ is marked with ~ (tilde symbol) thereabove will be described as σ(tilde).

β$_j$, K(tilde), X(tilde)$_{jk}$ and σ(tilde)$_k$ included in Equation (4) can be represented by Equations (5). The machine learning unit 401 provided in the computer 400 calculates Equations (5) in advance. A calculation result is incorporated in the logic circuit included in the analysis unit 11. b and K(tilde) included in Equation (4) are constants, β$_j$ and σ(tilde)$_k$ are vectors, and X(tilde)$_{jk}$ is a matrix.

[Math. 5]

$$\beta_j = \alpha_j Y_j, \tilde{K} = -\frac{1}{K^2}, \tilde{X}_{jk} = \hat{X}_{jk} + \frac{\mu_k}{\sigma_k}, \tilde{\sigma}_k = \frac{1}{\sigma_k} \quad (5)$$

FIG. 26(*a*) shows a discriminant calculation circuit of the above-described Equation (4). A calculation time is shortened by calculating the addition of k included in Equation (4) in parallel. By shortening the calculation time, the analysis unit 11 can shorten a time required for classification of the observed object 5.

FIG. 26(*b*) shows a discriminant calculation circuit for calculating the above-described Equation (4) at a higher speed. In the discriminant calculation circuit shown in FIG. 26(*b*), in addition to the configuration in which the above-described addition of k is subjected to parallel processing, the addition of j included in Equation (4) is subjected to parallel processing for calculation. As a result, the analysis unit 11 can classify the observed object 5 at a higher speed than in the discriminant calculation circuit shown in FIG. 26(*a*).

Although a method of implementing the support vector machine technique in the discriminant calculation circuit has been described above, the classification algorithm of the classification unit 101 is not limited thereto.

Next, an example when the analysis device performs machine learning of the observed object 5 observed in flow cytometry will be described.

Figure 27:
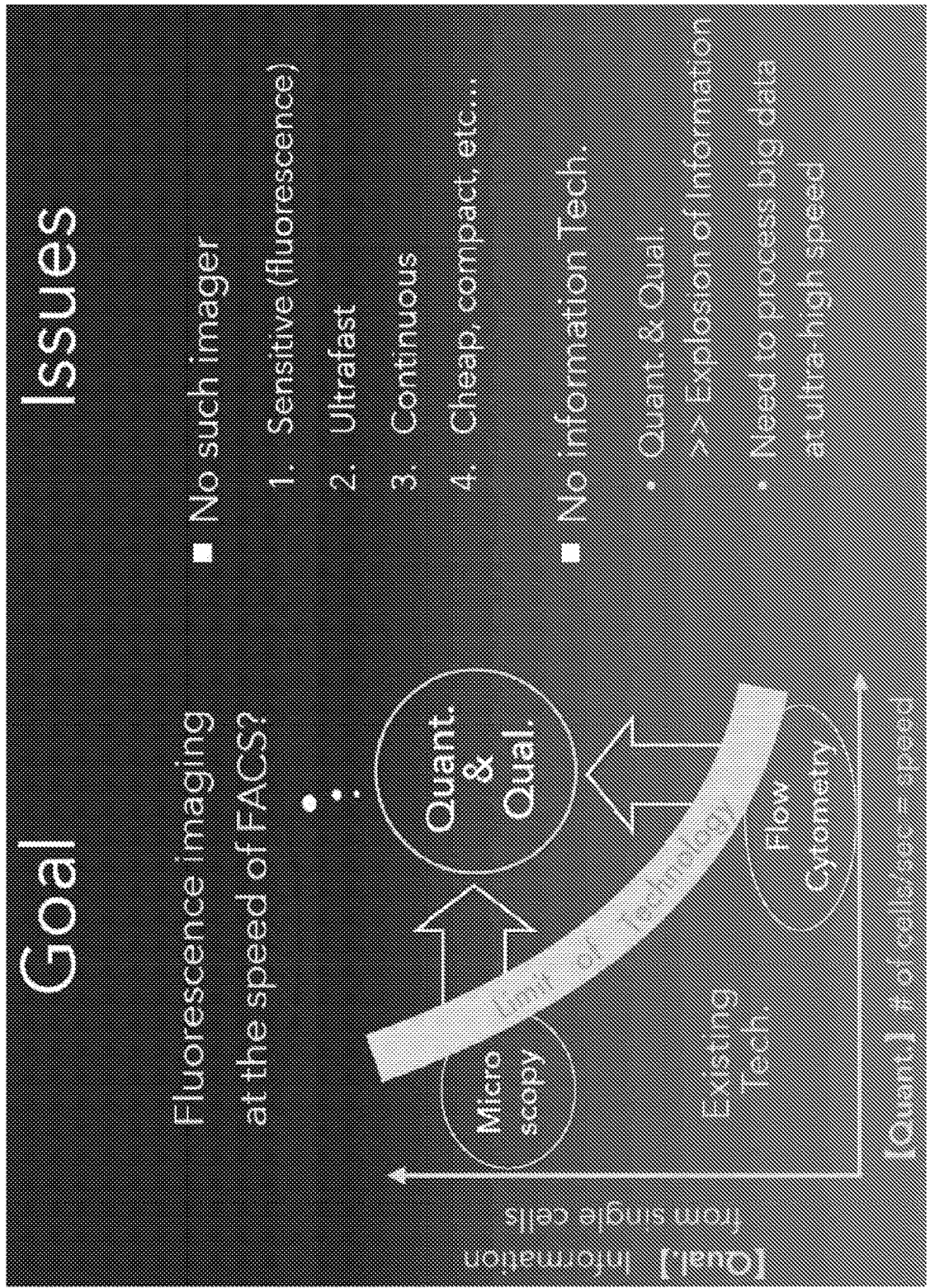
FIG. 27 is a diagram showing conventional cytometry.

FIG. 27 is a diagram showing conventional cytometry. Conventional cytometry has a problem that it is difficult to observe the observed object at a high speed and change the measurement method for each measurement purpose.

Figure 28:
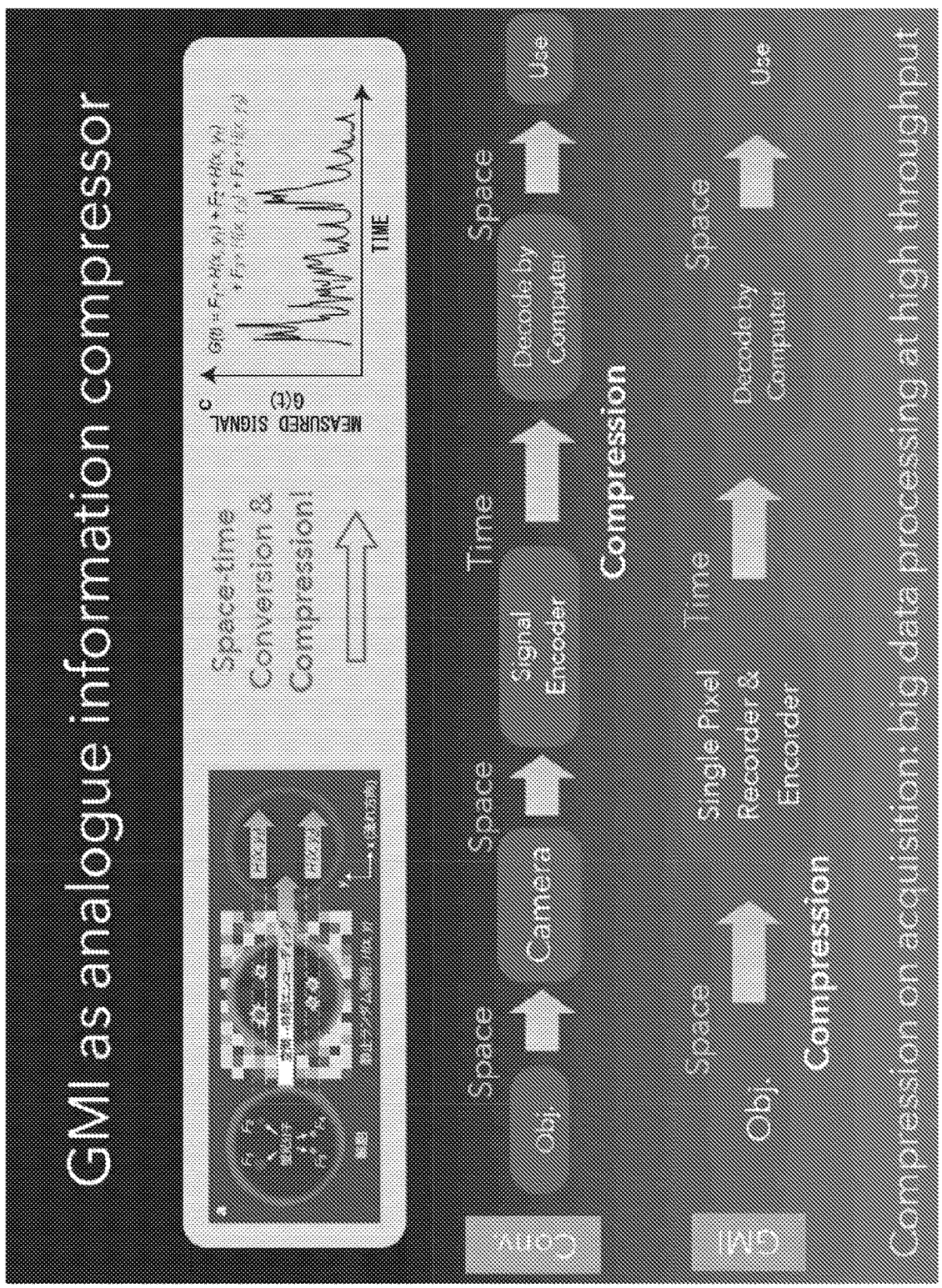
FIG. 28 is a diagram showing an example of a processing method for observing an observed object of a GMI method.

FIG. 28 is a diagram showing an example of a processing method for observing the observed object of the GMI method that solves the above-described problem. In the GMI method, pattern illumination is radiated to an observed object such as a cell moving along a flow path. The observed object irradiated with the pattern illumination emits electromagnetic waves. The electromagnetic waves emitted from the observed object are detected. Also, the pattern illumination radiated to the cells may be illumination for radiating uniform light. If the observed object is irradiated with the uniform light, the GMI method causes the electromagnetic waves emitted from the observed object to be transmitted through a pattern structure having a plurality of regions having different electromagnetic wave transmission characteristics. In the GMI method, the electromagnetic waves transmitted through the pattern structure are detected.

Figure 29:
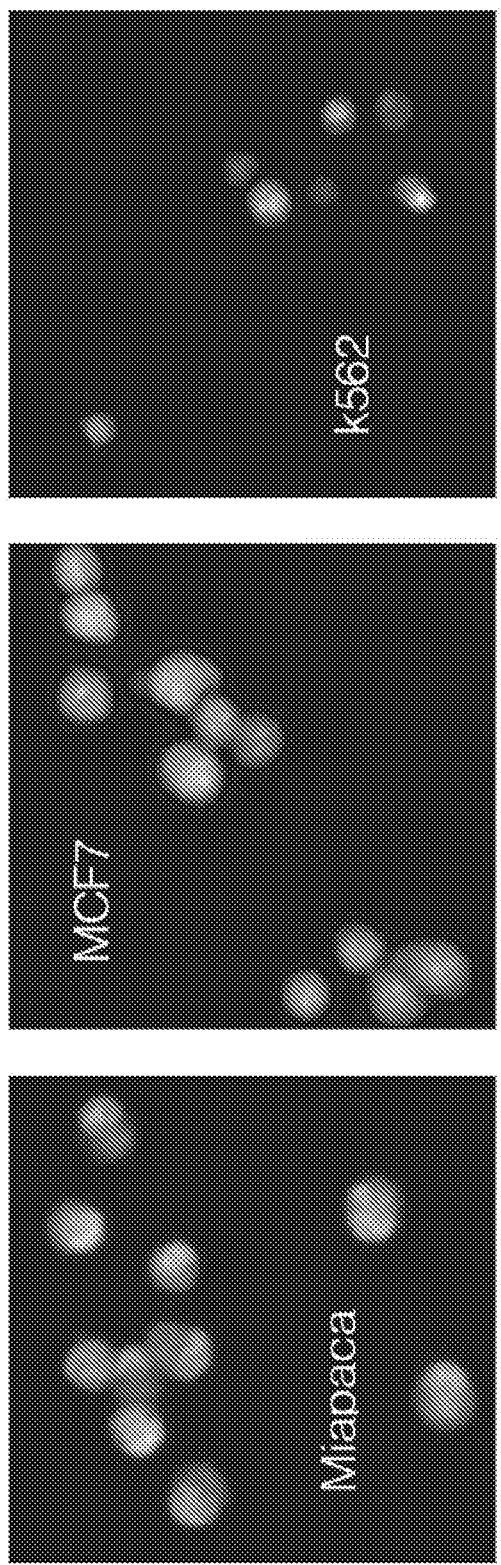
FIG. 29 is a diagram showing a concept of the GMI method.

FIG. 29 shows a concept thereof. A time required for image reconstruction and feature quantity extraction and analysis from the image is shortened by directly applying machine learning to the temporal waveform signal and a processing speed is significantly shortened by analyzing compressed small data as it is.

Figure 30:
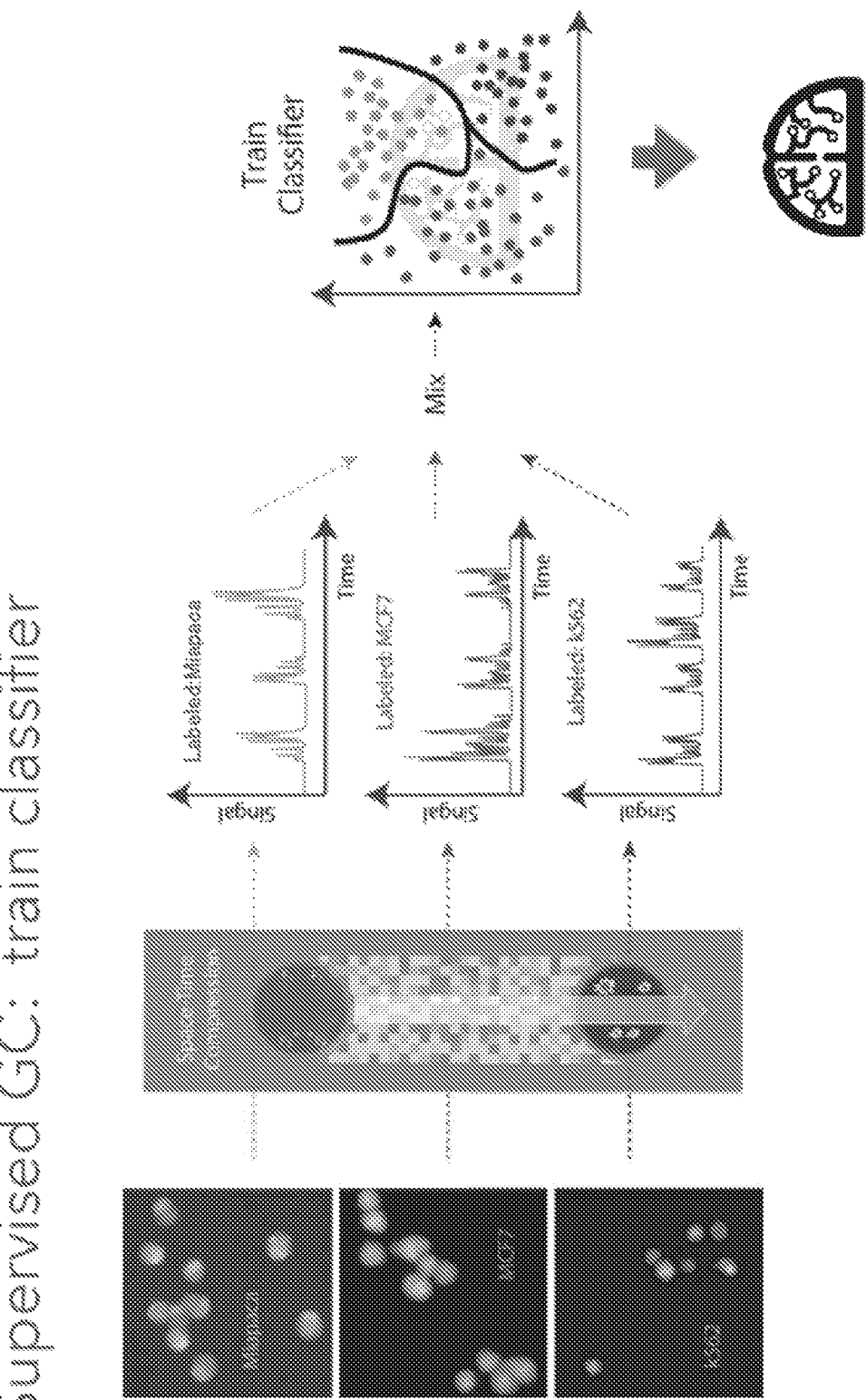
FIG. 30 is a diagram showing three types of cell specifically used.

From FIG. 30, specific implementation examples in cell classification are shown.

FIG. 30 shows three types of cells specifically used. Miapaca and MCf7 have similar sizes and similar characteristics and k562 has a smaller size. All are dyed green by dead cell staining (LIVE/DEAD Fixable Green Dead Cell Stain Kit, for 488 nm excitation, Thermo Fisher scientific) and classified using machine learning. Only MCF7 is subjected to nuclear staining (DAPI) in blue and this is used for verification of classification accuracy thereafter.

FIG. 30 shows a method of forming a classifier. Miapaca, MCF7, and k562 are separately moved along a flow path, and a temporal waveform signal is generated during imaging based on a GMI method. Threshold value processing is performed on the generated signal and each cell type label is attached thereto. A waveform signal group with this cell type label is incorporated into the computer and a classifier for classifying the waveform signal group is formed. As a classifier formation method, a support vector machine method is applied.

Figure 31:
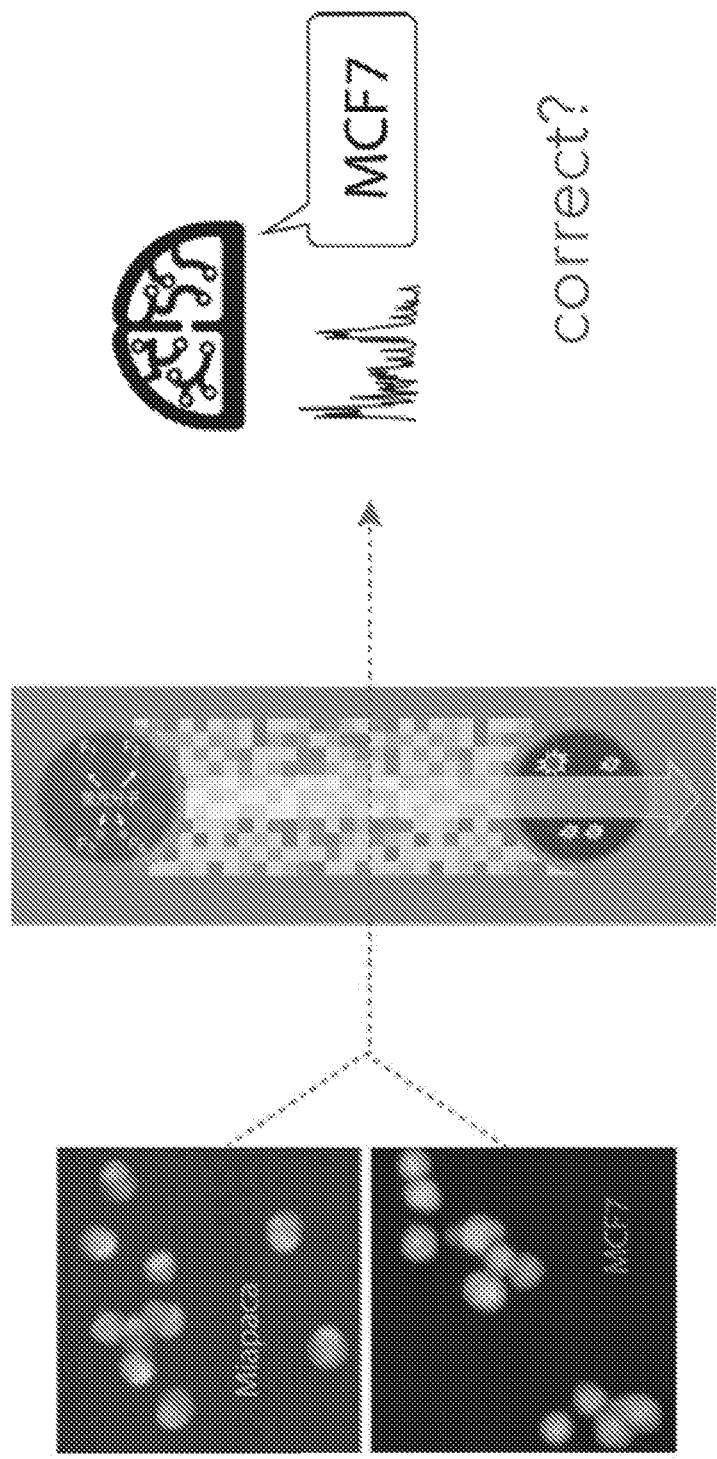
FIG. 31 is a diagram showing an example of a method of forming a classifier.

Next, different cell types (here, MCF7 and Miapaca) shown in FIG. 31 are experimentally mixed, cell classification is performed on the temporal waveform signal generated according to GMI using a previously provided classifier, and verification of the classification result is performed according to a total of DAPI signal intensities.

Figure 32:
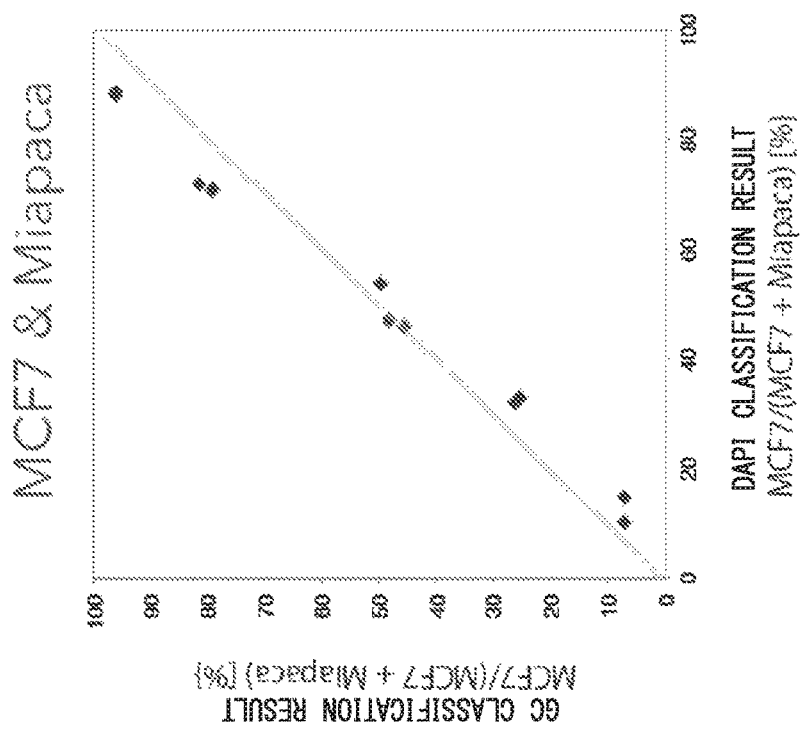
FIG. 32 is a diagram showing an example of a result of classifying different cell types.

FIG. 32 shows a result thereof. A concentration of MCF7 using machine learning classification for a temporal waveform of a green fluorescence signal is shown with respect to a concentration of MCF7 according to DAPI (blue, correct answer) classification when the concentration of MCF7 in a mixed liquor is changed and a correct answer is shown with high accuracy (>87%). When MCF7 and Miapaca are compared in a green fluorescence image, it is difficult to perform classification with the human eye and the usefulness of machine learning is obvious. High-speed and high-accuracy cell classification implementation has been demonstrated.

Figure 33:
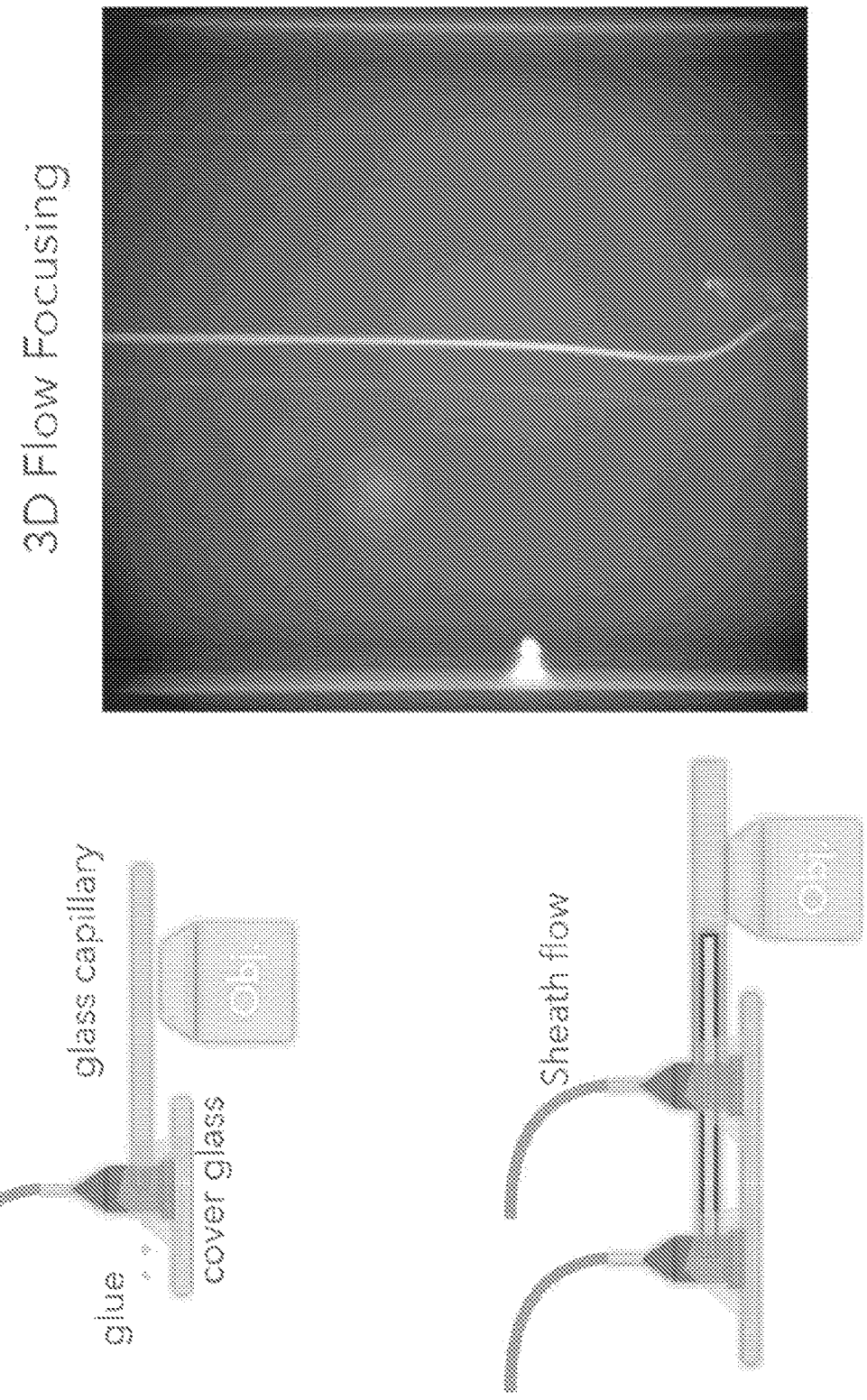
FIG. 33 is a diagram showing an example of a fluid system in flow cytometry implementation.
Figure 34:
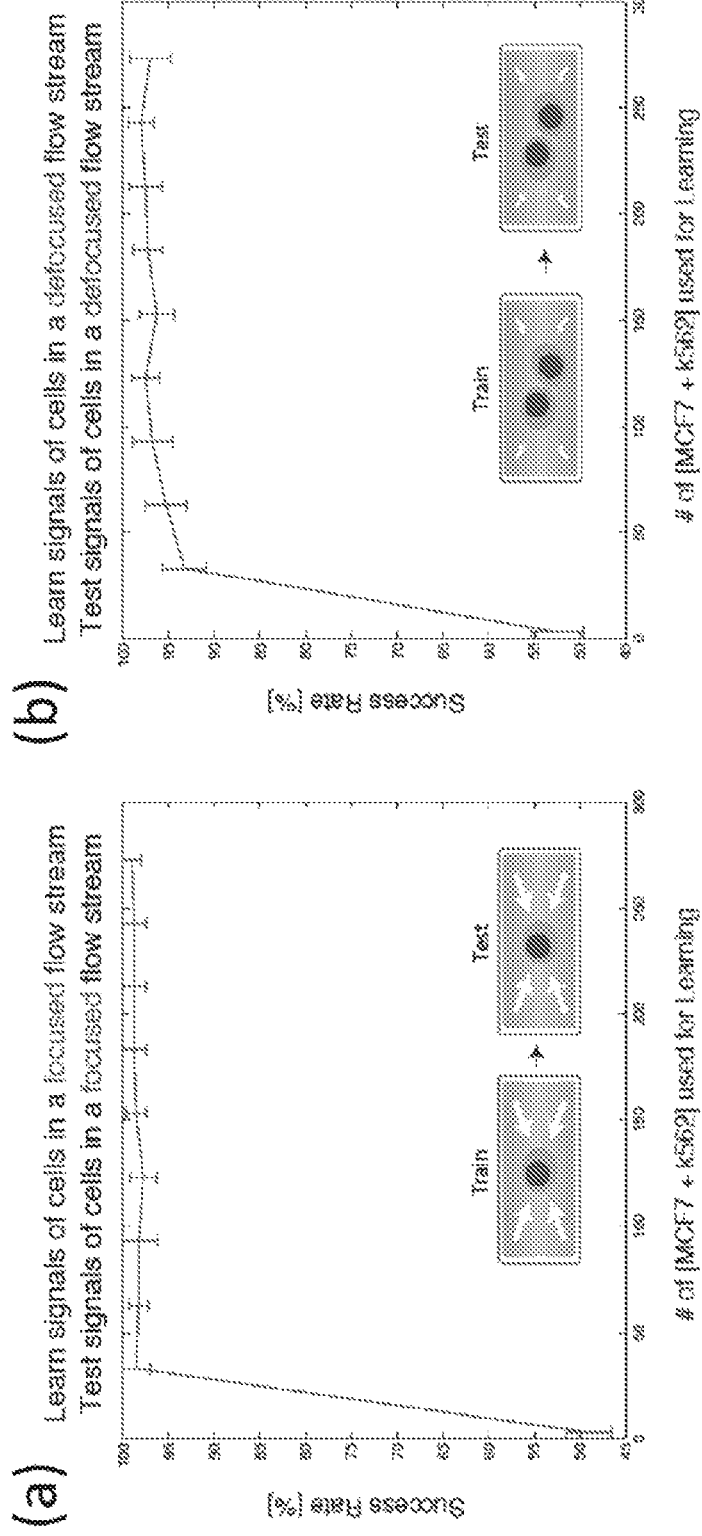
FIG. 34 is a diagram showing an example of classification accuracy in an ideal fluid experiment system.
Figure 35:
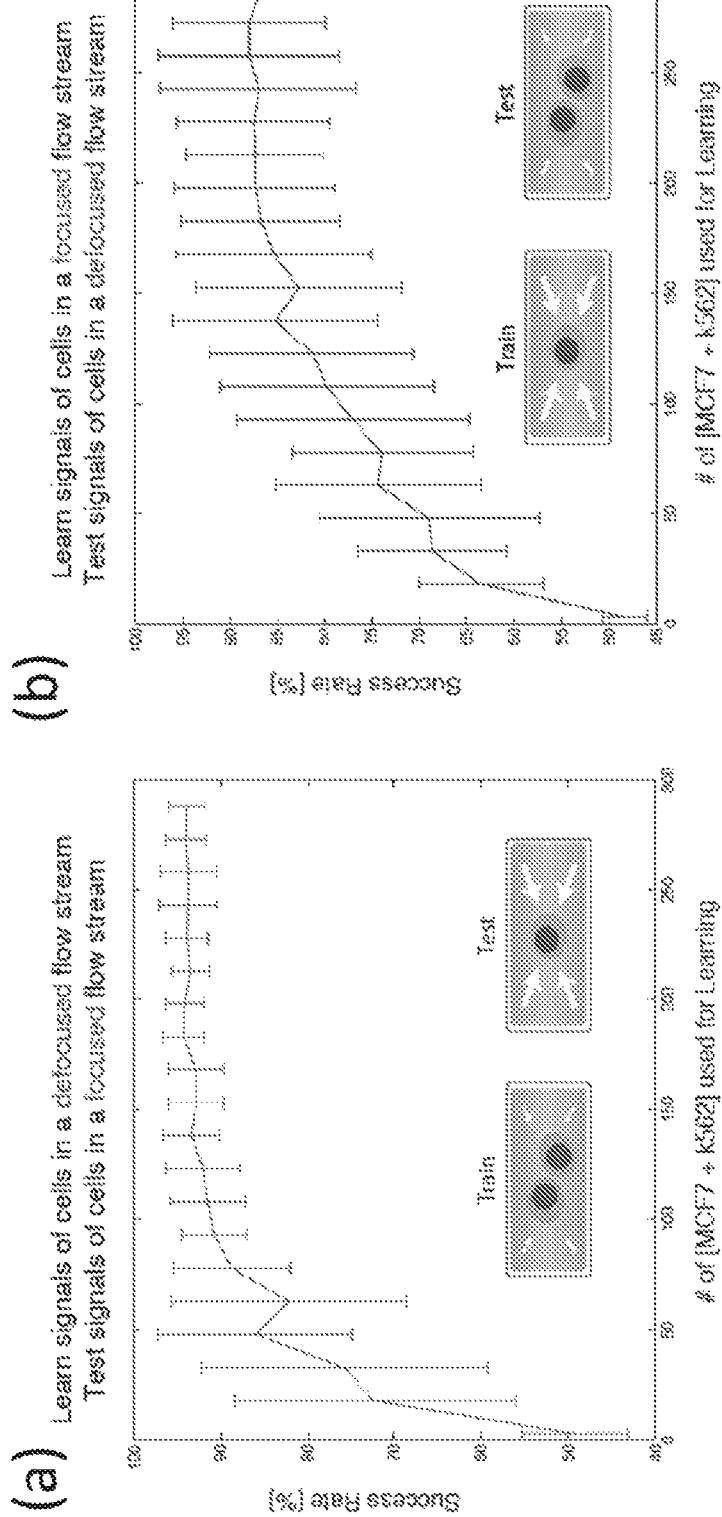
FIG. 35 is a diagram showing an example of classification accuracy in a robust classification method.

Further, FIGS. 33 to 35 show an example in which a fluid system is implemented in flow cytometry implementation. Here, although the above-described cell classification accuracy when the fluid experimental system is changed was verified, no correct answer was given according to an intensity of a DAPI signal and a temporal waveform group with a cell type label was incorporated into the computer and was classified (without teaching the correct answer to the machine) and accuracy was verified. As shown in FIG. 8, it is generally known that it is possible to align cells at the same width (fluctuation) on the same stream line using microfluidic engineering (a flow focusing method).

In FIGS. 34 and 35, an extent to which classification accuracy is improved with respect to the number of temporal waveforms used for learning when a fluid system is changed is plotted. Also, a cell temporal waveform to be learned uses randomly mixed cells. In an ideal fluid experiment system, the cells flow through the same streamline and generate a very uniform GMI temporal waveform. At this time, as shown in FIG. 34(*a*), the classification accuracy sharply increases and reaches about 98%. On the other hand, as shown in FIG. 34(*b*), when a flow focus is relaxed and a width is given to the streamline, the increase in accuracy becomes moderately gentle and the accuracy achieved also slightly decreases, but an accuracy of more than 95% can be still achieved. However, in practical application of fluid experiments, there are vibrations of the flow path, instability of the optical system, and the like and a robust classification method is required. At this time, if learning is performed with the waveform signal when the flow focus is relaxed and a waveform signal with an enhanced follow focus is classified, a classification accuracy of about 90% can be robustly obtained as shown in FIG. 35(*a*) and the accuracy is also stable. On the other hand, as shown in FIG. 35(*b*), when learning is performed in a waveform signal when the flow focus is enhanced and a waveform signal with a relaxed flow focus is classified, the classification accuracy does not reach 90% and the accuracy is also unstable. From this, it was shown that generalization of machine learning can be implemented and practicality can be improved by performing learning with a greater breadth of data. Also, in the experiment shown in FIG. 7 described above, data with the enhanced flow focus and data with the relaxed flow focus are mixed and used for learning.

In other words, when the flow focus is enhanced and tested on the basis of teacher information obtained through learning of after the flow focus is relaxed, the most robust classification accuracy can be obtained. On the other hand, when the flow focus is enhanced and tested on the basis of the teacher information obtained through learning of after the flow focus is enhanced, the most accurate classification accuracy can be obtained if the conditions are uniform.

Also, when testing is performed on the basis of teacher information obtained by combining data learned by relaxing the flow focus and data learned by enhancing the flow focus, robust and accurate classification accuracy can be obtained.

In other words, the analysis device mechanically learns the observed object 5 in accordance with a flow line width adjusted by the flow path width adjusting unit provided in the flow cytometer 300. In the following description, the flow line width will be also described as a flow path width. The analysis device can perform more accurate and robust classification by analyzing the observed object 5 on the basis of teaching information obtained by combining mechanically learned data in a state in which the flow line width is wider than a diameter of the observed object 5 and mechanically learned data in a state in which the flow line width is a flow line width according to the diameter of the observed object 5.

An analysis device of the present embodiment includes a flow path along which an observed object is able to move; a light-emitting unit configured to emit light radiated to a light irradiation region of the flow path; a pattern structure unit having a plurality of regions whose light transmission characteristics are different; a flow path width control unit configured to variably control a movable flow path width of the observed object which moves along the flow path; a detection unit configured to detect electromagnetic waves emitted from the observed object irradiated with the light on the basis of a region and relative movement within the flow path of the light and the observed object by radiating the light to the observed object of the light irradiation region; an acquisition unit configured to acquire a change in an intensity of the electromagnetic waves detected by the detection unit over time as an observed result signal indicating a state of the observed object when the light is radiated to the observed object; a teacher information generation unit configured to generate teacher information indicating a criterion for classifying the state of the observed object using machine learning on the basis of the observed result signal acquired by the acquisition unit and a flow path width when the observed result signal is acquired; and an estimation unit configured to estimate the state of the observed object which moves along the flow path on the basis of the observed result signal acquired by the acquisition unit and the teacher information generated by the teacher information generation unit.

Also, in the analysis device, the flow path width control unit provided in the analysis device may control the flow path width so that the flow path width becomes a first flow path width which is a width according to a diameter of the observed object, the teacher information generation unit may generate first teacher information based on a first observed result signal detected by the detection unit as the teacher information in the first flow path width controlled by the flow path width control unit, and the estimation unit may estimate the state of the observed object which moves along the flow path on the basis of the first teacher information generated by the teacher information generation unit and the observed result signal acquired by the acquisition unit.

Also, in the analysis device, the flow path width control unit provided in the analysis device may control the flow path width so that the flow path becomes a second flow path width which is a width based on the diameter of the observed object and is wider than the first flow path width, the teacher information generation unit may further generate second teacher information based on a second observed result signal detected by the detection unit as teacher information in the second flow path width controlled by the flow path width control unit, and the estimation unit may estimate the state of the observed object which moves along the flow path on the basis of the first teacher information generated by the teacher information generation unit, the second teacher information generated by the teacher information generation unit, and the observed result signal acquired by the acquisition unit.

Also, in the analysis device, the flow path width control unit provided in the analysis device may control the flow path width so that the flow path width becomes the first flow path width which is the width based on the diameter of the observed object and has a narrower width than the second flow path width, the teach information generation unit may further generate the first teacher information based on the first observed result signal detected by the detection unit in the first flow path width controlled by the flow path width control unit, and the estimation unit may estimate the state of the observed object which moves along the flow path on the basis of the first teacher information generated by the teacher information generation unit, the second teacher information generated by the teacher information generation unit, and the observed result signal acquired by the acquisition unit.

REFERENCE SIGNS LIST

1 Light source
3 Light irradiation region
5 Observed object
7 Light-receiving unit
9 Storage unit
11 Analysis unit
13 Optical system control unit
21 Plurality of light regions
25 Light-receiving region
31 Flow cell
33 Sorting unit
200 Analysis system
300 Flow cytometer
400 Computer
401 Machine learning unit

The invention claimed is:
1. A method for analyzing one or more observed objects, comprising:
(a) providing an analysis device comprising (i) a light-receiving unit comprising a sensor and (ii) a logic circuit operatively coupled to the light-receiving unit;
(b) using the sensor to (i) receive at least one electromagnetic wave from the one or more observed objects and

(ii) convert the at least one electromagnetic wave into one or more time-series electrical signals; and (c) using the logic circuit to analyze the one or more time-series electrical signals to classify or recognize at least one target object among the one or more observed objects without generation of an image, wherein the one or more time-series electrical signals comprise one or more compressed temporal signals comprising spatial information corresponding to the observed objects.

2. The method of claim 1, wherein (b) further comprises illuminating the one or more observed objects with light from a light source to yield the at least one electromagnetic wave.

3. The method of claim 2, further comprising controlling or adjusting one or more properties of the light based at least in part on an analysis result of the logic circuit.

4. The method of claim 2, wherein the light illuminating the one or more observed objects comprises a structured illumination pattern having a plurality of regions with different optical characteristics.

5. The method of claim 1, wherein (c) further comprises using a classification algorithm to analyze the time-series electrical signals, wherein the classification algorithm is updated based at least in part on an analysis result of the logic circuit.

6. The method of claim 1, wherein the one or more observed objects comprise one or more unlabeled objects, and wherein classifying or recognizing the one or more target objects among the one or more observed objects comprises classifying or recognizing one or more target objects among the one or more unlabeled objects using a classification model.

7. The method of claim 6, wherein the classification model is trained prior to (c) by applying machine learning directly to one or more time-series electrical signals obtained from one or more labeled objects.

8. The method of claim 1, wherein the light-receiving unit comprises a single-pixel detection element.

9. The method of claim 1, wherein the light-receiving unit comprises a structured detection system, wherein the structured detection system comprises a plurality of regions having different optical characteristics.

10. The method of claim 1, wherein in (c), the one or more observed objects comprise one or more cells.

11. The method of claim 1, wherein the one or more observed objects are undergoing a relative motion with respect to a light irradiation region at which the one or more observed objects are illuminated.

12. The method of claim 1, wherein the at least one electromagnetic wave comprises at least one of scattered light, Raman scattering, transmitted light, or fluorescent light.

13. The method of claim 1, further comprising, subsequent to (c), sorting one or more target objects based at least in part on a classification or recognition of the one or more target objects among the one or more observed objects.

14. The method of claim 1, further comprising using an optical element to illuminate the one or more observed objects with a structured illumination pattern as the one or more observed objects move relative to the structured illumination pattern, wherein the optical element is disposed along a light path between a light source used to illuminate the one or more observed objects and a light irradiation region at which the one or more observed objects are illuminated.

15. The method of claim 1, further comprising using an optical element to receive the at least one electromagnetic wave from the one or more observed objects as the one or more observed objects move relative to the optical element, wherein the optical element is disposed along a light path between a light irradiation region at which the one or more observed objects are illuminated and the light-receiving unit.

16. The method of claim 1, further comprising adjusting a flow line width along which the one or more observed objects are moving.

17. The method of claim 16, wherein the one or more observed objects are recognized, classified, or sorted using a classification model, wherein the classification model is trained by applying machine learning directly to the one or more time-series electrical signals, which time-series electrical signals comprise one or more signals obtained for at least one flow line width which is different from the flow line width along which the one or more observed objects are moving.

18. The method of claim 6, wherein a classification label indicating the observed object is attached to each of one or more time-series electrical signals, and the classification model is trained prior to (c) by applying machine learning directly to the one or more time-series electrical signals obtained from one or more observed objects.

19. The method of claim 7, wherein the one or more labeled objects are labeled with a fluorescent label.

20. The method of claim 6, wherein the classification model is created by supervised machine learning in combination with unsupervised machine learning.

* * * * *